(12) United States Patent
Riis et al.

(10) Patent No.: US 10,934,070 B2
(45) Date of Patent: *Mar. 2, 2021

(54) ANTI-SCALPING PHARMACEUTICAL PACKAGING FILM

(71) Applicant: BEMIS COMPANY, INC., Neenah, WI (US)

(72) Inventors: Jennifer L. Riis, Neenah, WI (US); Yuan Liu, Neenah, WI (US); Lyndsey A. McMillan, Neenah, WI (US); Christopher L. Osborn, Germantown, WI (US); Rishabh Jain, Appleton, WI (US)

(73) Assignee: Bemis Company, Inc., Neenah, WI (US)

( * ) Notice: Subject to any disclaimer, the term of this patent is extended or adjusted under 35 U.S.C. 154(b) by 233 days.

This patent is subject to a terminal disclaimer.

(21) Appl. No.: 15/115,993

(22) PCT Filed: Feb. 10, 2015

(86) PCT No.: PCT/US2015/015246

§ 371 (c)(1),
(2) Date: Aug. 2, 2016

(87) PCT Pub. No.: WO2015/123211

PCT Pub. Date: Aug. 20, 2015

(65) Prior Publication Data

US 2017/0174405 A1    Jun. 22, 2017

Related U.S. Application Data

(63) Continuation-in-part of application No. 14/178,005, filed on Feb. 11, 2014.

(51) Int. Cl.

| | |
|---|---|
| *B65D 65/40* | (2006.01) |
| *B32B 15/085* | (2006.01) |
| *B32B 27/08* | (2006.01) |
| *B32B 27/36* | (2006.01) |
| *B32B 27/32* | (2006.01) |
| *A61K 9/70* | (2006.01) |
| *A61K 31/465* | (2006.01) |
| *A61K 31/4468* | (2006.01) |
| *B32B 7/12* | (2006.01) |
| *B32B 27/10* | (2006.01) |
| *B32B 27/34* | (2006.01) |
| *A61K 31/167* | (2006.01) |
| *B65B 9/06* | (2012.01) |
| *B65D 65/14* | (2006.01) |
| *B32B 27/30* | (2006.01) |
| *A61K 31/565* | (2006.01) |

(52) U.S. Cl.
CPC ............ *B65D 65/40* (2013.01); *A61K 9/703* (2013.01); *A61K 9/7023* (2013.01); *A61K 31/167* (2013.01); *A61K 31/4468* (2013.01); *A61K 31/465* (2013.01); *A61K 31/565* (2013.01); *B32B 7/12* (2013.01); *B32B 15/085* (2013.01); *B32B 27/08* (2013.01); *B32B 27/10* (2013.01); *B32B 27/308* (2013.01); *B32B 27/32* (2013.01); *B32B 27/325* (2013.01); *B32B 27/34* (2013.01); *B32B 27/36* (2013.01); *B65B 9/06* (2013.01); *B65D 65/14* (2013.01); *B32B 2255/10* (2013.01); *B32B 2255/26* (2013.01); *B32B 2307/31* (2013.01); *B32B 2307/70* (2013.01); *B32B 2307/7244* (2013.01); *B32B 2307/7246* (2013.01); *B32B 2439/40* (2013.01); *B32B 2439/80* (2013.01); *Y10T 428/31797* (2015.04)

(58) Field of Classification Search
CPC .. A61K 9/7023; A61K 31/465; A61K 31/565; B32B 7/12; B32B 27/08; B32B 27/10; B32B 27/325; B32B 2255/26; B32B 2307/31; B32B 2307/7244; B32B 2439/40; B32B 2307/7246
See application file for complete search history.

(56) References Cited

U.S. PATENT DOCUMENTS

| | | |
|---|---|---|
| 3,635,376 A | 1/1972 | Hellstrom et al. |
| 3,809,221 A | 5/1974 | Compere |
| 3,912,081 A | 10/1975 | Haines et al. |
| 3,912,082 A | 10/1975 | Gerner et al. |
| 4,211,326 A | 7/1980 | Hein et al. |
| 4,294,361 A | 10/1981 | Margulies et al. |
| 4,884,693 A | 12/1989 | Brutsch |
| 5,203,470 A | 4/1993 | Brown |
| 5,218,049 A | 6/1993 | Yamamoto et al. |
| 5,469,968 A | 11/1995 | Matthews et al. |
| 5,532,030 A | 7/1996 | Hirose et al. |
| 5,712,031 A | 1/1998 | Kelch et al. |
| 5,758,774 A | 6/1998 | Leblong |
| 5,783,273 A | 7/1998 | Yamamoto et al. |

(Continued)

FOREIGN PATENT DOCUMENTS

| | | |
|---|---|---|
| EP | 0481471 A1 | 4/1992 |
| EP | 1283224 A1 | 2/2003 |
| EP | 1300238 A3 | 4/2003 |
| EP | 1398149 B1 | 3/2004 |
| EP | 1602350 A1 | 12/2005 |

(Continued)

OTHER PUBLICATIONS

Liang, Zou et al., "Applications on Solubility Parameter Theory in the Pharmaceutical Field", Journal of Chengdu University of TCM, Dec. 2007, pp. 46-51, vol. 30, No. 4, Chengdu, China.

(Continued)

*Primary Examiner* — Fred M Teskin

(57) ABSTRACT

A film for packaging a product that has a pharmaceutical active agent includes a product-contacting sealing layer. The product contacting layer includes at least 90 wt. % of an ethylene norbornene copolymer having a glass transition temperature in a range from 50° C. to 110° C. The pharmaceutical active agent comprises a Hansen Solubility Parameter for the product-contacting sealing layer of 0.5 or greater.

11 Claims, 2 Drawing Sheets

(56) References Cited

U.S. PATENT DOCUMENTS

| | | | |
|---|---|---|---|
| 5,862,915 A | 1/1999 | Plezia et al. |
| 5,876,814 A | 3/1999 | Oda et al. |
| 5,894,930 A | 4/1999 | Faughey et al. |
| 5,897,941 A | 4/1999 | Shah |
| 6,006,913 A | 12/1999 | Ludemann et al. |
| 6,041,929 A | 3/2000 | Brunner et al. |
| 6,383,592 B1 | 5/2002 | Lowry et al. |
| 6,546,281 B1 | 4/2003 | Zhang et al. |
| 6,632,910 B2 | 10/2003 | Takagi et al. |
| 6,682,797 B1 | 1/2004 | Otoi et al. |
| 6,705,467 B1 | 3/2004 | Kancsar et al. |
| 6,746,743 B2 | 6/2004 | Knoerzer et al. |
| 6,969,740 B2 | 11/2005 | Klosiewicz |
| 7,063,211 B2 | 6/2006 | Williams-Hartman |
| 7,129,296 B2 | 10/2006 | Van Dun et al. |
| 7,189,300 B2 | 3/2007 | Knoerzer et al. |
| 7,243,798 B2 | 7/2007 | Buss |
| 7,288,316 B2 | 10/2007 | Jester |
| 7,365,130 B2 | 4/2008 | Rivett et al. |
| 7,383,671 B2 | 6/2008 | Conti |
| 7,416,768 B2 | 8/2008 | Knoerzer et al. |
| 7,497,623 B2 | 3/2009 | Thomas et al. |
| 7,608,317 B2 | 10/2009 | Keckeisen et al. |
| 7,686,513 B2 | 3/2010 | Knoerzer et al. |
| 7,829,633 B2 | 11/2010 | Heukelbach et al. |
| 7,854,225 B2 | 12/2010 | Pasbrig et al. |
| 7,919,171 B2 | 4/2011 | Young |
| 7,919,174 B2 | 4/2011 | Ruokolainen et al. |
| 8,003,179 B2 | 8/2011 | Merical et al. |
| 8,056,716 B2 | 11/2011 | Fonteyne et al. |
| 8,092,877 B2 | 1/2012 | Jester et al. |
| 8,206,796 B2 | 6/2012 | Opusko et al. |
| 8,377,529 B2 | 2/2013 | Bekele |
| 8,574,694 B2 | 11/2013 | Neill et al. |
| 8,863,967 B2 | 10/2014 | Suzuki et al. |
| 2002/0012781 A1 | 1/2002 | Beer et al. |
| 2002/0061982 A1 | 5/2002 | Donald et al. |
| 2003/0236352 A1 | 12/2003 | Winowiecki |
| 2005/0037162 A1 | 2/2005 | Adams |
| 2005/0186373 A1 | 8/2005 | Rhee et al. |
| 2005/0244665 A1 | 11/2005 | Rivett et al. |
| 2005/0260366 A1 | 11/2005 | Magnusson |
| 2006/0000734 A1 | 1/2006 | Ninomiya et al. |
| 2006/0027480 A1 | 2/2006 | Buss |
| 2006/0046006 A1 | 3/2006 | Bastion et al. |
| 2006/0062946 A1 | 3/2006 | Beer et al. |
| 2006/0198973 A1 | 9/2006 | Jester |
| 2006/0249422 A1 | 11/2006 | Bates |
| 2006/0283758 A1 | 12/2006 | Pasbrig |
| 2007/0054142 A1 | 3/2007 | Lee et al. |
| 2007/0202337 A1 | 8/2007 | Lischefski et al. |
| 2007/0212539 A1 | 9/2007 | Yamada et al. |
| 2007/0221534 A1 | 9/2007 | Intini |
| 2007/0224379 A1 | 9/2007 | Stevenson |
| 2007/0259142 A1 | 11/2007 | Lischefski et al. |
| 2007/0278114 A1 | 12/2007 | Kane et al. |
| 2008/0067099 A1 | 3/2008 | Young |
| 2008/0075901 A1 | 3/2008 | Lee et al. |
| 2008/0118749 A1 | 5/2008 | Aubee et al. |
| 2008/0227900 A1 | 9/2008 | Borke et al. |
| 2008/0251411 A1 | 10/2008 | Walker et al. |
| 2008/0280117 A1 | 11/2008 | Knoll et al. |
| 2008/0286547 A1 | 11/2008 | Hubbard et al. |
| 2008/0311370 A1 | 12/2008 | Tatarka |
| 2009/0020898 A1 | 1/2009 | Goerlitz et al. |
| 2009/0042026 A1 | 2/2009 | Pasbrig |
| 2009/0081439 A1 | 3/2009 | Lischefski et al. |
| 2009/0110888 A1 | 4/2009 | Wuest et al. |
| 2009/0123611 A1 | 5/2009 | Bekele |
| 2009/0183744 A1 | 7/2009 | Hayton et al. |
| 2009/0208685 A1 | 8/2009 | Rivers et al. |
| 2009/0285511 A1 | 11/2009 | Aithani |
| 2009/0310890 A1 | 12/2009 | Suzuki et al. |
| 2009/0324911 A1 | 12/2009 | Li et al. |
| 2010/0009208 A1 | 1/2010 | Lee |
| 2010/0121290 A1 | 5/2010 | Rasmussen et al. |
| 2010/0127073 A1 | 5/2010 | van Esch |
| 2010/0163446 A1 | 7/2010 | Suzuki et al. |
| 2010/0279132 A1 | 11/2010 | Niederst |
| 2011/0005961 A1 | 1/2011 | Leplatois et al. |
| 2011/0049003 A1 | 3/2011 | Bellamah et al. |
| 2011/0101342 A1 | 5/2011 | Kim et al. |
| 2011/0104342 A1 | 5/2011 | Glaser et al. |
| 2011/0158564 A1 | 6/2011 | Krumme |
| 2011/0174651 A1 | 7/2011 | Kimball |
| 2011/0198261 A1 | 8/2011 | Kurtze et al. |
| 2011/0262589 A1 | 10/2011 | Safarik |
| 2012/0006707 A1 † | 1/2012 | Krumme |
| 2012/0101209 A1 | 4/2012 | Khanna et al. |
| 2012/0107542 A1 | 5/2012 | Nelson et al. |
| 2012/0152954 A1 | 6/2012 | Bruehl et al. |
| 2012/0199509 A1 | 8/2012 | McKiel, Jr. et al. |
| 2013/0085244 A1 | 4/2013 | Zhao et al. |
| 2013/0189617 A1 | 7/2013 | Merical et al. |
| 2013/0243894 A1 | 9/2013 | Schirmer |
| 2014/0308466 A1 | 10/2014 | Kashima et al. |
| 2015/0125098 A1 | 5/2015 | Okamoto et al. |
| 2015/0225151 A1 | 8/2015 | Osborn et al. |
| 2015/0283029 A1 | 10/2015 | Riis et al. |
| 2015/0298439 A1 | 10/2015 | Osborn et al. |
| 2017/0081099 A1 | 3/2017 | Priscal et al. |

FOREIGN PATENT DOCUMENTS

| | | | |
|---|---|---|---|
| EP | 1827283 A1 | 9/2007 |
| EP | 2468661 A1 | 6/2012 |
| EP | 2796524 A1 | 10/2014 |
| EP | 2803713 A1 | 11/2014 |
| JP | H11268087 A | 10/1999 |
| JP | H11286087 A | 10/1999 |
| JP | 2007098579 A | 4/2007 |
| JP | 2007156348 A | 6/2007 |
| JP | 2010077391 A | 4/2010 |
| JP | 2012003221 A | 1/2012 |
| JP | 2013135414 A | 7/2013 |
| JP | 2013249070 A | 12/2013 |
| WO | 9827925 A1 | 7/1998 |
| WO | 1998055537 | 12/1998 |
| WO | 200226494 A2 | 4/2002 |
| WO | 2004032990 A2 | 4/2004 |
| WO | 2007104513 A1 | 9/2007 |
| WO | 2008101946 A2 | 8/2008 |
| WO | 2009098261 A1 | 8/2009 |
| WO | 2009105205 A1 | 8/2009 |
| WO | 2012037180 A1 | 3/2012 |
| WO | 2013096078 A1 | 6/2013 |
| WO | 2013105524 A1 | 7/2013 |
| WO | 2013116445 A1 | 8/2013 |
| WO | 2014088585 A1 | 6/2014 |
| WO | 2015123211 A1 | 8/2015 |
| WO | 2017114922 A1 | 7/2017 |

OTHER PUBLICATIONS

Zeon Corporation, "Cyclo Olefin Polymer (COP): Zeonor®", retrieved online Jan. 21, 2016, at http://www.zeon.co.ip/content/200181692.pdf.

TOPAS® Advanced Polymers Brochure TB003 "Medical" Jan. 2007.

TOPAS® Advanced Polymers Brochure "Packaging" pp. 1-32.

Sajilata, M. G., K. Savitha, & V. R. Kanetkar "Scalping of Flavors in Packaged Foods", MS20060142, Sep. 18, 2006.

Jester, Randy, "Add a Layer of COC to Boost Polyolefin Film Properties", Plastics Technology, retrieved online Jan. 27, 2014 at www.ptonline.com/articles/add-a-layer-of-COC-to-boost-polyolefin-film-properties.

Jester, Randy, "Cyclic Olefin Copolymer Enhances Ployolefin Blends for Film Packaging", Plastics Technology, retrieved online Jan. 27, 2014 at www.ptonline.com/articles/cyclic-olefin-copolymer-enhances-ployolefin-blends-for-film-packaging.

Drug Information Online, retrieved Apr. 8, 2013 at http://www.drugs.com/pro/nicotine-patch.html.

(56) References Cited

OTHER PUBLICATIONS

Jester, Randy, Conference Paper, "TOPAS® Cyclic Olefin Copolymers in Food Packaging—High Aroma Barrier combined with Low Extractables", 2005 PLACE Conference.
Jester, Randy, "Heat Seal Characteristics of Cyclic Olefin Copolymer / Polyethylene Blends", slides 1-18, presented by Randy D. Jester in Sep. 2002 at the TAPPI 2002 PLACE Conference, Boston Massachusetts.
Hansen, Charles M., "Hansen Solubility Parameters; A User's Handbook", p. 8, 29, 272, and 263, Second Edition, CRC Press, 2007.
Ackermann, Dr. Joachim, "Third party submission according to Art. 115 EPC; European patent application No. 15 705 765.4-1303", p. 1-8, Jul. 19, 2017.
Tucker, Nesha, Milliken & Company, "Advancements in PE Nucleation", slides 1-27, SPI Future of Film and Bag Conference, Power Point presentation, May 17, 2011.
Horrocks, Martin and Chris Kerscher, "A Novel Nucleating Agent for Polyethylene", p. 29-39, Plastics and Rubber Singapore Journal, 2008.
William, Todd G., Equistar Chemicals LP, "Variables That Affect/ Control High Density Polyethylene Film Oxygen/Moisture Barrier", p. 1-9, article presented at ANTEC 2003, Nashville, TN, May 4-8, 2003.
Ferrell, Michael William, letter RE: U.S. Appl. No. 14/178,005 and PCT Patent Application Serial No. PCT/US2015/015246, dated Apr. 1, 2016, pp. 1-54, USA.
Ackermann, Dr. Joachim, "Third party submission according to Art. 115 EPC; European patent application No. 15 105 765A", p. 1-4, Mar. 5, 2019.
Ferrell, Michael William, letter RE: United States Patent Application U.S. Appl. No. 15/115,993 entitled Anti-Scalping Pharmaceutical Packaging Film and United States Patent Application U.S. Appl. No. 14/178,005 entitled Anti-Scalping Transdermal Patch Packaging Film, dated Mar. 15, 2019, pp. 1-2, USA.
Tollefson, Brian k, "Transmittal of Third-Party Submission Documents", RE: U.S. Appl. No. 15/115,993, dated Apr. 3, 2019, pp. 1-14, USA.
Hatke, Wilfried Dr., "Affidavit", dated Mar. 18, 2019, p. 1, including referenced Topas 2011 Cyclic Olefin Copolymer (COC) brochure titled "Packaging", dated Apr. 2011, pp. 2-33.
Way Back Machine capture of "Transdermal patch", Wikipedia, dated Apr. 13, 2010, pp. 1-4.
Topas "Packaging", Advanced Polymers Catalogue, Jul. 2013, pp. 1-28.
Gungor, S. M., Swedef Erdal and Yildiz Ozsoy, "Plasticizers in Transdermal Drug Delivery Systems", available as a pen access article in 2012 under www.intechopen.com., pp. 91-112.
Herrlich et al., "Solvent Bonding of Polymer Combinations for Micromedical Applications", Proc. 2011 Int. Conf. on Microtechnologies in Medicine and Biology, Lucerne, Switzerland, 4-6 May, 2011, pp. 265-266.
Hanson, Charles M., "Hansen Solubility Parameters", https://www.hansen-solubility.com/contents/Hsp%200CT%202009.ppt and https://www.hansensolubility.com/contents/Text%20for%20HSP%20PowerY020Point20Presentation, pdf available in Oct. 2009; see also https://www.hansensolubility.com/downloads.php.
Scheler, Stefan; Alfred Fahr and Xiangli Liu "Linear combination methods for prediction of drug skin permeation", Admet & DMPK 2(4) (2014), published Jan. 9, 2015, pp. 199-220.
Bausch, Dr. Thorsten, "Third Party Observations According to Article 115 EPC; European patent application No. 15705765.4", p. 1-21, Jun. 12, 2019.
The Wayback Machine capture of the Wikipedia page including the Wikipedia entry for the keyword "Transdermal Patch", Apr. 13, 2010.†
Topas 2011 Cyclic Olefin COpolymer (COC) brochure named "Packaging", Apr. 2011.†

† cited by third party

ANTI-SCALPING PHARMACEUTICAL PACKAGING FILM

RELATED APPLICATION

This application is a national stage application of International Patent Application No. PCT/US15/15246, filed on Feb. 10, 2015, which is a continuation-in-part to U.S. patent application Ser. No. 14/178,005, filed on Feb. 11, 2014, entitled ANTI-SCALPING TRANSDERMAL PATCH PACKAGING FILM, which is hereby incorporated herein by reference to the extent that it does not conflict with the present disclosure.

FIELD

The present application relates generally to packaging suitable for packaging an article for collecting or administering a physiologically active substance such as transdermal drug delivery patches.

TECHNICAL BACKGROUND

Pharmaceuticals such as the drugs fentanyl and nicotine are often administered through the use of transdermal patches which are applied to a patient's skin to permit drug delivery over time by absorption. Prior to application of a drug containing patch, the patch is packaged in a pouch which is designed to be opened to permit access to the patch by the patient or caregiver for application to a patient's skin. Suitable packaging for transdermal patches should contain the patch and its drug within the package while protecting the patch from contamination and deleterious effects from the external environment. Thus, articles such as a pouch may hold a transdermal patch to protect the patch and its drug contents from contact or exposure to unwanted materials such as microbes, insects, air, moisture, sunlight, etc. The container is typically sealed e.g. by a heat seal to provide a hermetic barrier.

The materials used in constructing transdermal patch packaging and especially the patch contact package interior surface layer should resist migration of chemicals between the patch and the package materials. Such migration of the drug or patch components from the patch to the package structure is referred to as "scalping". A common material employed for transdermal patch package interior surface layers that prevents scalping is polyacrylonitrile which is often sold under the Barex® trademark by Ineos AG. While Barex® has superb antiscalping properties it is very expensive, poor tear properties that make pouch opening difficult, and has limited availability which creates supply chain risk because of its manufacture on only a single production reactor. Other polymers used in transdermal patch packaging as a surface contact layer include polyester. Polyester suffers from the disadvantage of being less resistant to scalping of certain chemicals than desired and its tear properties are also less than desired. Accordingly, there is a need for a more cost efficient packaging material for containing articles for collecting or administering a physiologically active substance such as transdermal drug delivery patches.

BRIEF SUMMARY

This disclosure, among other things, relates to films for packaging products containing a pharmaceutical active agent. The films resist migration of chemicals, such as pharmacological active agents or excipients, between the product and the film. Thus, the films are anti-scalping films. In a packaged product, the anti-scalping layer can be in contact with the pharmaceutical active agent. As used herein, "in contact with the pharmaceutical active agent," in the context of a layer of a film, means that under typical storage conditions some portion of the active agent will contact the layer. The active agent may be in direct contact with the product contacting layer or may be in indirect contact with the layer. Indirect contact between the active agent and the product contacting layer can occur, for example, due to volatilization of the active agent or an active agent carrier within the package to cause the active agent, which is not stored in direct contact with the product contacting layer, to contact the layer. However, even if the active agent is not in contact with the sealing layer, it may be desirable for the sealing layer to be anti-scalping to provide assurance that if an active agent accidentally became exposed to the sealing layer, the sealing layer would not substantially scalp the active agent.

The product contacting layers of the films described herein include at least 90 wt. % of an ethylene norbornene copolymer having a glass transition temperature in a range from 50° C. to 138° C. Layers having such properties were found to resist migration of nicotine and fentanyl. These results were unexpected because ethylene norbornene copolymers, like polyethylene, are polyolefins, and because polyethylene has been previously shown to have poor anti-scalping properties.

Polymers are typically compared based on their polymer classification. Accordingly, because polyethylene was determined to be a poor choice for an anti-scalping film or layer, other polyolefins would be expected to be poor choices as well. These expectations were bolstered by the fact that cyclic olefin copolymers (COCs), such as ethylene norbornene copolymers, perform similarly to linear low density polyethylene with regard to d-limonene. See, for example, 2005 PLACE Conference, September 27-29, Las Vegas, Nev., slide show entitled "TOPAS® Cyclic Olefin Copolymers in Food Packaging—High Aroma Barrier Combined with Low Extractables, presented by Randy Jester, slide 10, available at http://www.slideshare.net/TopasAdvancedPolymers/aroma-barrier-web, which states, "Scalping of d-Limonene by COC is similar to that of LLDPE, indicating that the solubility of d-Limonene in COC is similar to that of LLDPE.". That is, COCs and linear low density polyethylene were determined to have poor anti-scalping performance with regard to d-limonene.

Following the unexpectedly good anti-scalping properties COCs as described herein with regard to nicotine and fentanyl, the anti-scalping properties of COCs with regard to other active pharmaceutical agents were evaluated to identify whether COCs may be useful as anti-scalping films or layers for these other active agents and to attempt to identify whether certain parameters can be used to predict whether COCs would be effective anti-scalping layers.

Without intending to be bound by theory, it is now believed that a combination of Hansen Solubility Parameter (HSP) of the pharmaceutical active agent and a film or layer comprising the ethylene norbornene copolymer and the glass transition temperature of the film or layer can be used to predict whether an ethylene norbornene copolymer film will have a suitable anti-scalping properties for a given pharmaceutical active agent.

In various embodiments, the pharmaceutical active agent has a HSP for the film or layer of 0.5 or greater and has a glass transition temperature of 50° C. or greater. The HSP is preferably 0.6 or greater, such as 0.7 or greater, 0.8 or greater, 0.9 or greater, or 1 or greater. Preferably, the glass transition temperature is 55° C. or greater, such as 60° C. or greater, or 65° C. or greater. In various embodiments, the glass transition temperature is 138° C. or less, such as 110° C. or less.

In some embodiments, the pharmaceutical active agent is selected from the group consisting of fentanyl, nicotine, lidocaine, estradiol, clonidine, ethinyl estradiol, oxybutynin, buprenorphine, granisitron, methylphenidate, and scopolamine.

In some embodiments, a flexible, multilayer packaging film suitable for packaging an article for collecting or administering a physiologically active substance such as transdermal drug delivery patches, oral dissolvable thin strips, and disposable, microfluidic test cassettes is provided having:
(a) an article contact layer having at least 90 wt. % of a norbornene ethylene copolymer and a glass transition temperature of from 65 to 110° C.;
(b) a poly olefin bulk layer;
(c) a first intermediate adhesive layer;
(d) an oxygen barrier layer having an oxygen transmission rate of less than less than 0.01 cm3/100 inches2/24 hours at 1 atmosphere and 23° C.;
(e) a second intermediate adhesive layer; and
(f) an exterior protective layer comprising a polymer selected from the group consisting of amorphous polyester, polyamide, polyolefin, nylon, polypropylene, or copolymers, or blends thereof;
wherein said multilayer film has the following properties: a WVTR of less than 0.01 g/100 inches$^2$ per 24 hours at Room Temperature (RT) (23° C.) and 1 atmosphere; and a thickness of 10 mil or less.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
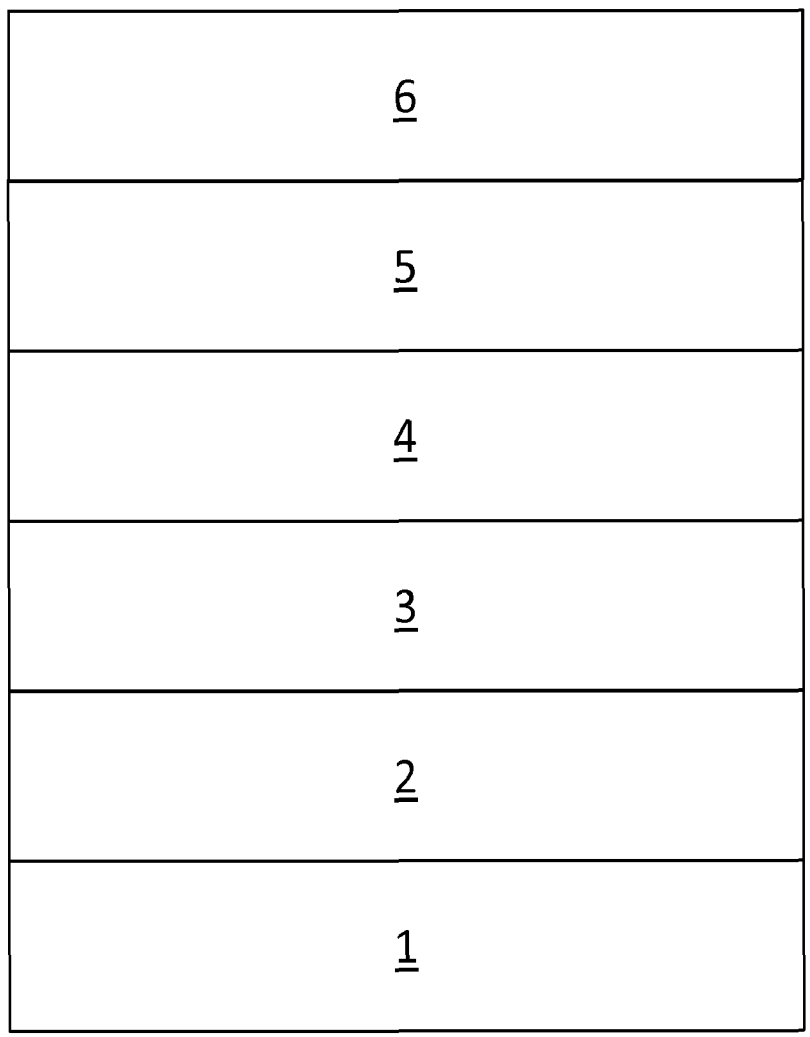
FIG. 1 is a schematic cross-sectional view of a multilayer film in accordance with embodiments presented herein.

The schematic drawings are not necessarily to scale. Like numbers used in the figures refer to like components. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Definitions and Nomenclature

In discussing polymer blends, plastic films and packaging, various acronyms are used herein and they are listed below. Also, in referring to blends of polymers a colon(:) will be used to indicate that the components to the left and right of the colon are blended. In referring to film structure, a slash "/" will be used to indicate that components to the left and right of the slash are in different layers and the relative position of components in layers may be so indicated by use of the slash to indicate film layer boundaries. Acronyms and terms commonly employed herein include:

APET—amorphous polyester terephthalate
OPET—biaxially oriented polyester terephthalate
COC—a cyclic olefin copolymer such as ethylene norbornene copolymer
PE—Polyethylene (ethylene homopolymer and/or copolymer of a major portion of ethylene with one or more α-olefins)
LDPE—low density polyethylene
LLDPE—linear low density polyethylene
mLLDPE—metallocene catalyzed linear low density polyethylene
$C_2$—ethylene monomer
$C_4$—butene-1 monomer
$C_6$—hexene-1 monomer
$C_8$—octene-1 monomer
$C_{10}$—decene-1 monomer
$C_2C_x$—a substantially linear copolymer of ethylene and an α-olefin where "x" indicates the number of carbon atoms in the comonomer.
VA—Vinyl Acetate
EVA—Copolymer of ethylene with vinyl acetate
EVOH—A saponified or hydrolyzed copolymer of ethylene and vinyl acetate
EAA—Copolymer of ethylene with acrylic acid
EMA—ethylene methacrylic acid copolymer ionomer—an ethylene-methacrylate acid copolymer whose acid groups have been neutralized partly or completely to form a salt, preferably a zinc or sodium salt
PVDC—Polyvinylidene chloride (also includes copolymers of vinylidene chloride, especially with vinyl chloride)

The term "nanocomposite" shall mean a mixture that includes a polymer, or copolymer having dispersed therein a plurality of individual platelets obtained from an exfoliated modified clay and having oxygen barrier properties.

The term "adhesive layer," or "tie layer," refers to a layer or material placed on one or more layers to promote the adhesion of that layer to another surface. Preferably, adhesive layers are positioned between two layers of a multilayer film to maintain the two layers in position relative to each other and prevent undesirable delamination. In some embodiments a peelable tie layer may be used which is designed to have either cohesive failure or delamination from one or both adjacent layers upon application of a suitable manual force to provide an opening feature for a package made from the film. Unless otherwise indicated, an adhesive layer can have any suitable composition that provides a desired level of adhesion with the one or more surfaces in contact with the adhesive layer material. Optionally, an adhesive layer placed between a first layer and a second layer in a multilayer film may comprise components of both the first layer and the second layer to promote simultaneous adhesion of the adhesive layer to both the first layer and the second layer to opposite sides of the adhesive layer.

As used herein, unless otherwise indicated, the phrases "seal layer," "'sealing layer,'" "heat seal layer," and "sealant layer," refer to a film layer, or layers, involved in the sealing of the film: to itself; to another film layer of the same film or another film; and/or to another article which is not a film e.g. a tray. In general, the sealant layer is a surface layer i.e. an exterior or an interior layer of any suitable thickness, that provides for the sealing of the film to itself or another layer. With respect to packages having only fin-type seals, as opposed to lap-type seals, the phrase "sealant layer" generally refers to the interior surface film layer of a package. The inside layer frequently can also serve as an article contact layer in the packaging of articles.

"Polyolefin" is used herein broadly to include polymers such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. Polyolefins may be made by a variety of processes well known in the art including batch and continuous processes using single, staged or sequential reactors, slurry, solution and fluidized bed processes and one or more catalysts including for example, heterogeneous and homogeneous systems and Ziegler, Phillips, metallocene, single site and constrained geometry catalysts to produce polymers having different combinations of properties. Such polymers may be highly branched or substantially linear and the branching, dispersity and average molecular weight and may vary depending upon the parameters and processes chosen for their manufacture in accordance with the teachings of the polymer arts.

"Polyethylene" is the name for a polymer whose basic structure is characterized by the chain—$(CH_2—CH_2—)_n$. Polyethylene homopolymer is generally described as being a solid which has a partially amorphous phase and partially crystalline phase with a density of between 0.915 to 0.970 g/cm$^3$. The relative crystallinity of polyethylene is known to affect its physical properties. The amorphous phase imparts flexibility and high impact strength while the crystalline phase imparts a high softening temperature and rigidity.

Unsubstituted polyethylene is generally referred to as high density homopolymer and has a crystallinity of 70 to 90 percent with a density between about 0.96 to 0.97 g/cm$^3$. Most commercially utilized polyethylenes are not unsubstituted homopolymer but instead have $C_2$-$C_8$ alkyl groups attached to the basic chain. These substituted polyethylenes are also known as branched chain polyethylenes. Also, commercially available polyethylenes frequently include other substituent groups produced by copolymerization. Branching with alkyl groups generally reduces crystallinity, density and melting point. The density of polyethylene is recognized as being closely connected to the crystallinity. The physical properties of commercially available polyethylenes are also affected by average molecular weight and molecular weight distribution, branching length and type of substituents.

People skilled in the art generally refer to several broad categories of polymers and copolymers as "polyethylene." Placement of a particular polymer into one of these categories of "polyethylene" is frequently based upon the density of the "polyethylene" and often by additional reference to the process by which it was made since the process often determines the degree of branching, crystallinity and density. In general, the nomenclature used is nonspecific to a compound but refers instead to a range of compositions. This range often includes both homopolymers and copolymers.

For example, "high density" polyethylene (HDPE) is ordinarily used in the art to refer to both (a) homopolymers of densities between about 0.960 to 0.970 g/cm$^3$ and (b) copolymers of ethylene and an α-olefin (usually 1-butene or 1-hexene) which have densities between 0.940 and 0.958 g/cm$^3$. HDPE includes polymers made with Ziegler or Phillips type catalysts and is also said to include high molecular weight "polyethylenes." In contrast to HDPE, whose polymer chain has some branching, are "ultra high molecular weight polyethylenes" which are essentially unbranched specialty polymers having a much higher molecular weight than the high molecular weight HOPE.

Hereinafter, the term "polyethylene" will be used (unless indicated otherwise) to refer to ethylene homopolymers as well as copolymers of ethylene with α-olefins and the term will be used without regard to the presence or absence of substituent branch groups. Another broad grouping of polyethylene is "high pressure, low density polyethylene" (LDPE). LDPE is used to denominate branched homopolymers having densities between 0.915 and 0.930 g/cm$^3$. LDPEs typically contain long branches off the main chain (often termed "backbone") with alkyl substituents of 2 to 8 carbon atoms.

Linear Low Density Polyethylene (LLDPE) are copolymers of ethylene with alpha-olefins having densities from 0.915 to 0.940 g/cm$^3$. The α-olefin utilized is usually 1-butene, 1-hexene, or 1-octene and Ziegler-type catalysts are usually employed (although Phillips catalysts are also used to produce LLDPE having densities at the higher end of the range, and metallocene and other types of catalysts are also employed to produce other well-known variations of LLDPEs). An LLDPE produced with a metallocene or constrained geometry catalyst is often referred to as "mLLDPE".

Ethylene α-olefin copolymers are copolymers having an ethylene as a major component copolymerized with one or more alpha olefins such as octene-1, hexene-, or butene-1 as a minor component. EAOs include polymers known as LLDPE, VLDPE, ULDPE, and plastomers and may be made using a variety of processes and catalysts including metallocene, single-site and constrained geometry catalysts as well as Ziegler-Natta and Phillips catalysts.

Very Low Density Polyethylene (VLDPE) which is also called "Ultra Low Density Polyethylene" (ULDPE) comprise copolymers of ethylene with α-olefins, usually 1-butene, 1-hexene or 1-octene and are recognized by those skilled in the art as having a high degree of linearity of structure with short branching rather than the long side branches characteristic of LDPE. However, VLDPEs have lower densities than LLDPEs. The densities of VLDPEs are recognized by those skilled in the art to range between 0.860 and 0.915 g/cm$^3$. Sometimes VLDPEs having a density less than 0.900 g/cm$^3$ are referred to as "plastomers".

Polyethylenes may be used alone, in blends and/or with copolymers in both monolayer and multilayer films for packaging applications.

As used herein, the term "modified" refers to a chemical derivative e.g. one having any form of anhydride functionality, such as anhydride of maleic acid, crotonic acid, citraconic acid, itaconic acid, fumaric acid, etc., whether grafted onto a polymer, copolymerized with a polymer, or otherwise functionally associated with one or more polymers, and is also inclusive of derivatives of such functionalities, such as acids, esters, and metal salts derived therefrom. Another example of a common modification is acrylate modified polyolefins.

As used herein, terms identifying polymers, such as e.g. "polyamide" or "polypropylene," are inclusive of not only polymers comprising repeating units derived from monomers known to polymerize to form a polymer of the named type, but are also inclusive of comonomers, as well as both unmodified and modified polymers made by e.g. derivitization of a polymer after its polymerization to add functional groups or moieties along the polymeric chain. Furthermore, terms identifying polymers are also inclusive of "blends" of such polymers. Thus, the terms "polyamide polymer" and "nylon polymer" may refer to a polyamide-containing homopolymer, a polyamide-containing copolymer or mixtures thereof.

The term "polyamide" means a high molecular weight polymer having amide linkages (—CONH—)$_n$ which occur along the molecular chain, and includes "nylon" resins which are well known polymers having a multitude of uses including utility as packaging films, bags, and pouches. See, e.g. Modern Plastics Encyclopedia, 88 Vol. 64, No. 10A, pp 34-37 and 554-555 (McGraw-Hill, Inc., 1987) which is hereby incorporated by reference. Polyamides are preferably selected from nylon compounds approved for use in producing articles intended for use in processing, handling, and packaging food or drugs.

The term "nylon" as used herein it refers more specifically to synthetic polyamides, either aliphatic or aromatic, either in crystalline, semi-crystalline, or amorphous form characterized by the presence of the amide group —CONH. It is intended to refer to both polyamides and co-polyamides.

Thus the terms "polyamide" or "nylon" encompass both polymers comprising repeating units derived from monomers, such as caprolactam, which polymerize to form a polyamide, as well as copolymers derived from the copolymerization of caprolactam with a comonomer which when polymerized alone does not result in the formation of a polyamide. Preferably, polymers are selected from compositions approved as safe for producing articles intended for use in processing, handling and packaging of food or drugs, such as nylon resins approved by the U.S. Food and Drug Administration provided at 21 CFR § 177.1500 ("Nylon resins"), which is incorporated herein by reference. Examples of these nylon polymeric resins for use in food or drug packaging and processing include: nylon 66, nylon 610, nylon 66/610, nylon 6/66, nylon 11, nylon 6, nylon 66T, nylon 612, nylon 12, nylon 6/12, nylon 6/69, nylon 46, nylon 6-3-T, nylon MXD-6, nylon MXDI, nylon 12T and nylon 6I/6T disclosed at 21 CFR § 177.1500. Examples of such polyamides include nylon homopolymers and copolymers such as those selected form the group consisting of nylon 4,6 (poly(tetramethylene adipamide)), nylon 6 (polycaprolactam), nylon 6,6 (poly(hexamethylene adipamide)), nylon 6,9 (poly(hexamethylene nonanediamide)), nylon 6,10 (poly(hexamethylene sebacamide)), nylon 6,12 (poly(hexamethylene dodecanediamide)), nylon 6/12 (poly(caprolactam-cododecanediamide)), nylon 6,6/6 (poly(hexamethylene adipamide-co-caprolactam)), nylon 66/610 (e.g., manufactured by the condensation of mixtures of nylon 66 salts and nylon 610 salts), nylon 6/69 resins (e.g., manufactured by the condensation of epsilon-caprolactam, hexamethylenediamine and azelaic acid), nylon 11 (polyundecanolactam), nylon 12 (polylauryllactam) and copolymers or mixtures thereof.

In use of the term "amorphous nylon copolymer," the term "amorphous" as used herein denotes an absence of a regular three-dimensional arrangement of molecules or subunits of molecules extending over distances which are large relative to atomic dimensions. However, regularity of structure may exist on a local scale. See, "Amorphous Polymers," Encyclopedia of Polymer Science and Engineering, 2nd Ed., pp. 789-842 (J. Wiley & Sons, Inc. 1985). In particular, the term "amorphous nylon copolymer" refers to a material recognized by one skilled in the art of differential scanning calorimetry (DSC) as having no measurable melting point (less than 0.5 cal/g) or no heat of fusion as measured by DSC using ASTM 3417-83. The amorphous nylon copolymer may be manufactured by the condensation of hexamethylenediamine, terephthalic acid, and isophthalic acid according to known processes. Amorphous nylons also include those amorpihous nylons prepared from condensation polymerization reactions of diamines with dicarboxylic acids. For example, an aliphatic diamine is combined with an aromatic dicarboxylic acid, or an aromatic diamine is combined with an aliphatic dicarboxylic acid to give suitable amorphous nylons.

As used herein, "EVOH" refers to ethylene vinyl alcohol copolymer. EVOH is otherwise known as saponified or hydrolyzed ethylene vinyl acetate copolymer, and refers to a vinyl alcohol copolymer having an ethylene comonomer. EVOH is prepared by the hydrolysis (or saponification) of an ethylene-vinyl acetate copolymer. The degree of hydrolysis is preferably from about 50 to 100 mole percent, more preferably, from about 85 to 100 mole percent, and most preferably at least 97%. It is well known that to be a highly effective oxygen barrier, the hydrolysjs-saponification must be nearly complete, i.e. to the extent of at least 97%. EVOH is commercially available in resin form with various percentages of ethylene and there is a direct relationship between ethylene content and melting point. For example, EVOH having a melting point of about 175° C. or lower is characteristic of EVOH materials having an ethylene content of about 38 mole % or higher. EVOH having an ethylene content of 38 mole % has a melting point of about 175° C. With increasing ethylene content the melting point is lowered. Also, EVOH polymers having increasing mole percentages of ethylene have greater gas permeabilities. A melting point of about 158° C. corresponds to an ethylene content of 48 mole %. EVOH copolymers having lower or higher ethylene contents may also be employed. It is expected that processability and orientation would be facilitated at higher contents; however, gas permeabilities, particularly with respect to oxygen, may become undesirably high for certain packaging applications which are sensitive to microbial growth in the presence of oxygen. Conversely lower contents may have lower gas permeabilities, but processability and orientation may be more difficult.

As used herein, the term "polyester" refers to synthetic homopolymers and copolymers having ester linkages between monomer units which may be formed by condensation polymerization methods. Polymers of this type are preferable aromatic polyesters and more preferable, homopolymers and copolymers of poly(ethylene terephthalate), poly(ethylene isophthalate), poly(butylene terephthalate), poly(ethylene naphthalate) and blends thereof. Suitable aromatic polyesters may have an intrinsic viscosity between 0.60 to 1.0, preferably between 0.60 to 0.80.

The terms "heat sealing layer" or "sealant layer" are used interchangeably to refer to a layer which is heat sealable i.e., capable of fusion bonding by conventional indirect heating means which generate sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling. Advantageously, the bond interface is preferably sufficiently thermally stable to prevent gas or liquid leakage therethrough when exposed to above or below ambient temperatures e.g. during one or more of the following: packaging operations, storage, handling, and transport. Heat seals may be designed to meet different conditions of expected use and various heat seal formulations are known in the art and may be employed with the present invention. Preferably the article contact or heat seal layer is heat sealable to itself, but may be sealable to other objects, films or layers e.g. to a tray when used as a lidding film, or to an outer layer in a lap seal or in certain tray overwrap embodiments.

As used herein, singular forms "a," "an" and "the" include plural referents unless the context clearly dictates otherwise. Thus, for example, reference to a "structured bottom surface" includes examples having two or more such "structured bottom surfaces" unless the context clearly indicates otherwise.

As used herein, the term "or" is generally employed in its sense including "and/or" unless the content clearly dictates otherwise. The term "and/or" means one or all of the listed elements or a combination of any two or more of the listed elements. The use of "and/or" in certain instances herein does not imply that the use of "or" in other instances does not mean "and/or".

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

For purposes of the present disclosure, recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a product contacting layer comprising an ethylene norbornene copolymer include embodiments where a product contacting layer consists of an ethylene norbornene copolymer and embodiments where a product contacting layer consists essentially of an ethylene norbornene copolymer.

Article Contact/Heat Sealing Layers

The films described herein have a product contact layer containing ethylene norbornene copolymer, which is a cyclic olefin copolymer (COC). COCs are commercially available from Topas as an amorphous, transparent copolymer of ethylene with norbornene made by polymerization with a metallocene catalyst. These commercially available COCs reportedly have high transparency and gloss, excellent moisture barrier and aroma barrier properties, a variable glass transition point between 50 and 178° C. (such as from 65 to 178° C.), high stiffness, high strength, excellent biocompatibility and inertness and easy to exclude and thermoform. COCs have previously been used for pharmaceutical, medical and food packaging applications including use in coextruded cast films for blister packaging and may be blended with polyethylene.

The product contacting layers of the films described herein include ethylene norbornene copolymers having a glass transition temperature ($T_g$) of 50-138° C. (such as 65-138° C.), an ethylene-norbornene comonomer content of 20-40 mole % ethylene and 30-60 mole % norbornene, or a glass transition temperature ($T_g$) of 50-138° C. (such as 65-138° C.) and an ethylene-norbornene comonomer content of 20-40 mole % ethylene and 30-60 mole % norbornene. In some embodiments, the product contacting layers of the films described herein comprise polymeric units derived from essentially only ethylene and norbornene comonomers.

In some embodiments, the product contacting layers of the films described herein include one or more of the following properties: a density ($\Delta$) of 1.02 g/cm$^3$; a melt volume ratio (MVR) of 1.0-12.0 cm$^3$/10 min. at 230° C., 2.16 kg load, and 1.0-2.0 at 190° C., 2.16 kg load (ISO 1133); a melt index of 0.1 to 1.9 at 190° C., 2.16 kg load (reported as calculated from ISO 1133 MVR using a melt density of 0.92). The product contacting layers of the films described herein can also include one or more other properties of Topas cyclic olefin copolyer described in a March 2006 brochure "Togas® Cylcic Olefin Copolymers" available from Topas Advanced Polymers on its website, which brochure is hereby incorporated by reference in its entirety.

In various embodiments, the contact layer can also function as a heat sealing or heat sealable layer to facilitate formation of hermetically sealed packages. The article contact layer comprises at least 90 wt. % of ethylene norbornene COC, more preferably at least 95 wt. %, and most preferably 100 wt. %. It may be blended with up to 10 wt. %, preferably up to 5 wt. % and more preferably up to 2.5 wt. % of compatible polymers such as polyolefins e.g. polyethylene, LLDPE, EAO copolymers, LDPE, colorants, processing aids and the like. Use of these polymers and components in a blend with the COC may undesirable affect the antiscalping properties of this layer and addition of amounts above 10 wt. % may be unacceptable for many applications of the film for packaging drugs or drug articles such as transdermal patches e.g. nicotine patches or fentanyl patches.

The terms "heat sealing layer" or "sealant layer" are used interchangeably to refer to a layer which is heat sealable i.e., capable of fusion bonding by conventional indirect heating means which generate sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling. Advantageously, the bond interface is preferably sufficiently thermally stable to prevent gas or liquid leakage therethrough when exposed to above or below ambient temperatures e.g. during one or more of the following: packaging operations, storage, handling, and transport.

Films and packaging described herein may include one or more additional optional layers, such as one or more barrier layers, an outer layer which can be an abuse-resistant outer layer, one or more intermediate layers, and one or more tie layers.

Barrier Layers

If included, a barrier layer preferably functions both as a gas barrier layer, and as a moisture barrier layer, although these functions may be provided by separate layers. A gas barrier layer is preferably an oxygen barrier layer, and is preferably a core layer positioned between and protected by surface layers. For example, an oxygen barrier layer can be in contact with a first surface layer and an adhesive layer or may be sandwiched between two tie layers and/or two surface layers.

An oxygen barrier is preferably selected to provide an oxygen permeability sufficiently diminished to protect the packaged article from undesirable deterioration or oxidative processes. For example, a film may comprise an oxygen barrier having an oxygen permeability that is low enough to prevent oxidation of oxygen sensitive articles and substances to be packaged in the film e.g. oxygen sensitive articles such as transdermal patches e.g. nicotine or fentanyl patches or oxygen sensitive collection samples such as blood which may be collected e.g. in a microcassette device. Preferably a multilayer packaging film in accordance with the present invention will have an oxygen barrier of less than or equal to 10 $cm^3$/100 $inches^2$/24 hours at 1 atmosphere and 23° C., more preferably less than 0.016 $cm^3/m^2$ per 24 hours at 1 atmosphere. To protect oxygen sensitive articles from deterioration from oxygen contact over time the films according to the present invention will have a preferred oxygen transmission rate ($O_2TR$) of less than 1, preferably less than 0.1, more preferably less than 0.01, and most preferably less than 0.001 g/100 $inches^2$ at 24 hours at Room Temperature (RT) (~23° C.) and 1 atmosphere (<0.001 $g/m^2$ at 24 hours at Room Temperature (RT) (~23° C.)) and 1 atmosphere).

A moisture barrier is preferably selected to provide a moisture permeability sufficiently diminished to protect the packaged article from undesirable deterioration. For example, a film may comprise a water barrier having a moisture permeability that is low enough to prevent deleterious effects upon packaged articles such as transdermal drug patches or other moisture sensitive products. A preferred film according to various embodiments will have a water or moisture transmission rate (WVTR) of less than 0.01 g/100 $inches^2$ per 24 hours at Room Temperature (RT) (23° C.) and 1 atmosphere. In some embodiments, a film has a WVTR of less than 0.01 g/100 $inches^2$ per 24 hours at Room Temperature (RT) (23° C.) and 1 atmosphere, or less than 0.001 g/100 $inches^2$ per 24 hours at Room Temperature (RT) (23° C.) and 1 atmosphere.

A barrier layer can comprise any suitable material. An oxygen barrier layer can comprise EVOH, polyvinylidene chloride, polyamide, polyester, polyalkylene carbonate, polyacrylonitrile, nanocomposite, a metallized film such as aluminum vapor deposited on a polyolefin, etc., as known to those of skill in the art. Suitable moisture barrier layers include aluminum foil, PVDC, or polyolefins such as LDPE or LLDPE. It is desirable that the thickness of the barrier layer be selected to provide the desired combination of the performance properties sought e.g. with respect to oxygen permeability, and delamination resistance, and water barrier properties. Suitable thicknesses in multilayer films are less than 15%, e.g. from 3 to 13% of the total film thickness and preferably less than about 10% of the total thickness of the multilayer film. Greater thicknesses may be employed however oxygen barrier polymers tend to be relatively expensive and therefore it is expected that less costly resins will be used in other layers to impart desirable properties once a suitable thickness is used to achieve the desired gas barrier property for the film layer combination. For example, the thickness of a core oxygen barrier layer may advantageously be less than about 0.45 mil (10.16 microns) and greater than about 0.05 mil (1.27 microns), including 0.10, 0.20, 0.25, 0.30, 0.40, or 0.45 mil thick.

An oxygen barrier layer of a film may comprise aluminum foil, or EVOH, although oxygen barrier layers comprising polyvinylidene chloride-vinyl chloride copolymer (PVDC or VDC-VC) or vinylidene chloride-methylacrylate copolymer (VDC-MA) as well as blends thereof, can also be used. One suitable EVOH barrier material is a 44 mol % EVOH resin E151B sold by Eval Company of America, under the trade name Evai® LC-E151B. Another example of an EVOH that may be acceptable can be purchased from Nippon Gohsei under the trade name Soarnol® AT (44 mol % ethylene EVOH).

For packaging of oxygen sensitive articles such as drug patches, an oxygen ($O_2$) permeability of less than about 310 $cm^3/m^2$ for a 24 hour period at 1 atmosphere, 0% relative humidity and 23° C., and preferably less than 75 $cm^3/m^2$, more preferably less than 20 $cm^3/m^2$. The thickness of the core layer may be varied and beneficially may be from about 0.05 to about 0.60 mils (1.3-15.2 microns).

A bulk layer may be provided to provide additional functionality such as stiffness or heat sealability or to improve machinability, cost, flexibility, barrier properties, etc. Preferred bulk layers comprise one or more polyolefins such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. The bulk layer may be of any suitable thickness from 0.1 to 7 mils or may even be omitted for use in certain applications, but is preferably present to improve especially stiffness/flexibility properties and heat sealability.

Abuse-Resistant Outer Layer

The films described herein may include an outer layer. Since it is seen by the user/consumer, in both monolayer and multilayer embodiments, the exterior surface of the film preferably has desirable optical properties and may preferably have high gloss. Also, it preferably withstands contact with sharp objects and provides abrasion resistance, and for these reasons it is often termed the abuse resistant layer. This exterior abuse-resistant layer may or may not also be used as a heat sealable layer. As the exterior surface layer of the film, this layer most often is also the exterior layer of any package, bag, pouch or other container made from the inventive film, and is therefore subject to handling and abuse e.g. from equipment during packaging, and from rubbing against other packages and shipping containers and storage shelves during transport and storage. This contact causes abrasive forces, stresses and pressures which may abrade away the film causing defects to printing, diminished optical characteristics or even punctures or breaches in the integrity of the package. Therefore the exterior surface layer is typically made from materials chosen to be resistant to abrasive and puncture forces and other stresses and abuse which the packaging may encounter during use. The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be heat resistance to burn through e.g. by impulse sealers or may be used as a heat sealing surface in certain package embodiments e.g. using overlap seals. The exterior layer may be tough to impart resistance to opening by children e.g. preventing the package from being opened by a child's bite. A preferred exterior child resistant layer comprise polyester film, preferably polyester terephthalate, preferably at least 0.9 mil in thickness. Suitable exterior surface layers may comprise: paper, oriented polyester, amorphous polyester, polyamide, polyolefin, cast or oriented nylon, polypropylene, or copolymers, or blends thereof. Oriented films of this or any other layer may be either uni-axially or bi-axially oriented. The exterior layer thickness is typically 0.5 to 2.0 mils. Thinner layers may be less effective for abuse resistance, however thicker layers, though more expensive, may advantageously be used to produce films having unique highly desirable puncture resistance and/or abuse resistance properties.

Intermediate Layers

An intermediate layer is any layer between the exterior layer and the interior layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, EMA, EAA, modified polyolefins e.g. anhydride grafted ethylene polymers, etc.

Tie Layers

In addition to the exterior layer, the interior layer, and intermediate layer such as a barrier layer, a multilayer packaging film can further comprise one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. In some embodiments, adhesive layers comprise materials found in both the first and second layers. The adhesive layer may suitably be less than 10% and preferably between 2% and 10% of the overall thickness of the multilayer film. Adhesive resins are often more expensive than other polymers so the tie layer thickness is usually kept to a minimum consistent with the desired effect. In one embodiment, a multilayer film comprises a multilayer structure comprising a first adhesive layer positioned between and in direct contact with the exterior layer and a core oxygen barrier layer; and preferably and optionally has a second tie layer between and in direct contact with the same core oxygen barrier layer and the interior layer to produce a five layer film. Adhesive layers may include modified e.g. anhydride modified polymers e.g. polyolefins such as polyethylenes or ethylene copolymers such as EVA and may also be primers or specialty adhesive resins.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

For example adhesive layers in contact with a layer comprising a polyester, such as PET, preferably comprise a suitable blend of polyolefins with other adhesive polymers. One preferred component of an adhesive layer in contact with a PET polyester layer is EMAC SP 1330 (which reportedly has: a density of 0.948 g/cm$^3$; melt index of 2.0 g/10 min.; a melting point of 93° C.; is at softening point of 49° C.; and a methylacrylate (MA) content of 22%).

The interior, exterior, intermediate or tie layers may be formed of any suitable thermoplastic materials, for example, polyamides, polystyrenes, styrenic copolymers e.g. styrenebutadiene copolymer, polyolefins, and in particular members of the polyethylene family such as LLDPE, VLDPE, HOPE, LDPE, ethylene vinyl ester copolymer or ethylene alkyl acrylate copolymer, polypropylenes, ethylene-propylene copolymers, ionomers, polybutylenes, alpha-olefin polymers, polyesters, polyurethanes, polyacrylamides, anhydride-modified polymers, acrylate-modified polymers, polylactic acid polymers, or various blends of two or more of these materials.

In another embodiment, the exterior, interior and/or one or more intermediate layers can comprise or consist essentially of a nylon blend composition. Preferably, the nylon blend composition comprises at least an amorphous nylon such as nylon 6I/6T copolymer, in combination with at least one semi-crystalline nylon homopolymer or copolymer such as nylon 6/12, 6/69, 6/66, MXD6, 6, 11, or 12.

In another embodiment of the invention one or more of the exterior, interior and/or one or more intermediate layers comprises at least one polyester polymer. Preferred polyester polymers comprise aromatic polyesters and more preferably, are homopolymers or copolymers of poly (ethylene terephthalate) (PET), poly (ethylene naphthalate) and blends thereof. Suitable polyesters may have an intrinsic viscosity of about 0.60 to about 1.2, preferably between 0.60 to 0.80. The polyester may be an aliphatic polyester resin, but is preferably an aromatic polyester resin. For example, polyester materials can be derived from dicarboxylic acid components, including terephthalic acid and isophthalic acid as preferred examples, and also dimers of unsaturated aliphatic acids. Examples of a diol component as another component for synthesizing the polyester may include: polyalkylene glycols, such as ethylene glycol, propylene glycol, tetramethylene glycol, neopentyl glycol, hexamethylene glycol, diethylene glycol, polyethylene glycol and polytetra methylene oxide glycol; 1,4-cyclohexane-dimethanol, and 2-alkyl-1,3-propanediol. More specifically, examples of dicarboxylic acids constituting the polyester resin may include: terephthalic acid, isophthalic acid, phthalic acid, 5-t-butyl-isophthalic acid, naphthalenedicarboxylic acid, diphenyl ether dicarboxylic acid, cyclohexane-dicarboxylic acid, adipic acid, oxalic acid, malonic acid, succinic acid, azelaic acid, sebacic acid, and dimer acids comprising dimers of unsaturated fatty acids. These acids may be used singly or in combination of two or more species. Examples of diols constituting the polyester resin may include: ethylene glycol, propylene glycol, tetramethylene glycol, neopentyl glycol, hexamethylene glycol, diethylene glycol, polyalkylene glycol, 1,4-cyclohexane-dimethanol, 1,4-butanediol, and 2-alkyl-1,3-propane diol. These diols may be used singly or in combination of two or more species.

Polyester compositions that comprise an aromatic polyester resin comprising an aromatic dicarboxylic acid component can be preferred in some aspects, including, e.g., polyesters between terephthalic acid (as a dicarboxylic acid) and diols having at most 10 carbon atoms, such as polyethylene terephthalate and polybutylene terephthalate. Particularly preferred examples thereof may include: copolyesters obtained by replacing a portion, preferably at most 30 mol %, more preferably at most 15 mol %, of the terephthalic acid with another dicarboxylic acid, such as isophthalic acid; copolyesters obtained by replacing a portion of the diol component such as ethylene glycol with another diol, such as 1,4-cyclohexane-dimethanol (e.g., "Voridian 9921", made by Voridian division of Eastman Chemical Co.); and polyester-polyether copolymers comprising the polyester as a predominant component (e.g., polyester-ether between a dicarboxylic acid component principally comprising terephthalic acid or/and its ester derivative and a diol component principally comprising tetramethylene glycol and tetramethylene oxide glycol, preferably containing the polytetra methylene oxide glycol residue in a proportion of 10-15 wt. %). It is also possible to use two or more different polyester resins in mixture. Examples of preferred polyesters are available under the trademarks Voridian 9663, Voridian 9921 and EAST AR® Copolyester 6763, all from Eastman Chemical Company, Kingsport, Tenn., U.S.A.

Optional Additives to Layers

Various additives may be included in the polymers utilized in one or more of the exterior, interior and intermediate or tie layers of packaging comprising the same. For example, a layer may be coated with an anti-block powder. Also, conventional anti-oxidants, antiblock additives, polymeric plasticizers, acid, moisture or gas (such as oxygen) scavengers, slip agents, colorants, dyes, pigments, organoleptic agents may be added to one or more film layers of the film or it may be free from such added ingredients. If the exterior layer is corona treated, preferably no slip agent will be used, but it will contain or be coated with an anti-block powder or agent such as silica or starch. Processing aides are typically used in amounts less than 10%, less than 7% and preferably less than 5% of the layer weight. A preferred processing aid for use in the outer layer of the film includes one or more of fluoroelastomers, stearamides, erucamides, and silicates.

Preferred films may also provide a beneficial combination of one or more or all of the properties including low haze, high gloss, good machinability, good mechanical strength and good barrier properties including high barriers to oxygen and water permeability. Suitable barrier properties may have values of WVTR less than or equal to 0.03 g/100 in$^2$/24 hours at 1 atmosphere and RT; and/or O$_2$TR values of less than or equal to 10 cm$^3$/100 in$^2$/24 hours at 1 atmosphere and RT. Preferred barrier property values are WVTR=<0.001 g/100 in$^2$/24 hours at 1 atmosphere and RT, and/or O$_2$TR values of less than or equal to 0.001 cm3/100 in$^2$/24 hours at 1 atmosphere and RT.

Methods of Manufacture

The inventive monolayer or multilayer film may be made by conventional processes. These processes to produce flexible films may include e.g. cast or blown film processes.

In some embodiments, the polymers defined herein are "unmodified" by any intentional grafting or copolymerization with modifying moieties such as dienes, rubber moieties or acrylic acids. However, the polymers may contain chemicals or additives in small amounts (typically under 1% by weight based on the weight of the polymer) which are present as byproducts of the polymer manufacturing process or otherwise added by polymer manufacturers including e.g. catalyst residues, antioxidants, stabilizers, antiblock materials and the like. In some embodiments, the polymers are "modified" or "derivatized" by grafting or copolymerization with modifying moieties. For purposes of the present disclosure, such modified or derivatized polymers are considered a subset of the polymer being modified. For example, a modified or derivatized polyethylene is considered a polyethylene.

Exact and Escorene polymers are the commercial designations of polymers available from Exxon Chemical Company of Houston, Tex., U.S.A. Afinity and Attane polymers are the commercial designations of polymers available from Dow Chemical Company of Midland, Mich., U.S.A. Surlyn and Elvax are the commercial designations of polymers available from Dupont, U.S.A.

Metal foils and metalized films are also contemplated. One or more functional properties may be contributed by one or more layers including desired levels of heat sealability, optical properties e.g. transparency, gloss, haze, abrasion resistance, coefficient of friction, tensile strength, flex crack resistance, puncture resistance, abrasion resistance, printability, colorfastness, flexibility, dimensional stability, barrier properties to gases such as oxygen, or to moisture, light of broad or narrow spectrum including e.g. uv resistance, etc. Preferred materials for use as container walls, pouch films, lidstock, include nylons, polyesters, polystyrenic polymers, and polyolefin e.g. ethylene or propylene homopolymers or copolymers, or mixtures thereof in any number of layers, particularly, but not limited to, one to nine or 14 layers or more. Preferred polyolefins include ethylene homopolymers or copolymers and may include low, medium, high and ultra-low or ultra-high density polymers. Examples are high density polyethylene (HDPE), ethylene alpha-olefin copolymers (EAO) preferably utilizing butene-1, hexene-1, or octene-1 comonomer with a predominate ethylene comonomer portion) and including e.g. linear low density polyethylene (LLDPE), very low density polyethylene (VLDPE), plastomers, elastomers, low density polyethylene (LDPE) copolymers of ethylene and polar groups such as vinyl acetate or ethyl acrylate e.g. ethylene vinyl acetate (EVA) or ethylene methyl acrylate (EMA) or ethylene acrylic acid copolymer (EAA), functional group modified polymers including e.g. anhydride modified EAOs. Propylene homopolymers and copolymers including polypropylene and propylene ethylene copolymer are useful. Gas diversion or container wall structures may also include a metal foil and may be a metal foil laminate with metal foil and a polymeric layer such as nylon. It may also be a metal foil laminate with an outer layer of polyethylene terephthalate, a core layer of metal foil and an inner layer of polyethylene. In this arrangement, the polyethylene terephthalate layer serves as a protective layer to the foil, and the polyethylene layer facilitates sealing. The foil is an excellent barrier to materials, organisms, oxygen, moisture and light.

In some embodiments, a packaging film as described herein may utilize a gas barrier layer such as aluminum foil, polyvinylidene chloride copolymers such as saran, or ethylene vinyl alcohol copolymers which provide high barriers to gas permeability.

In some embodiments, a packaging film as described herein may utilize a moisture barrier layer such as aluminum foil, polyvinylidene chloride copolymers such as saran, or polyolefin materials such as LDPE which impede moisture vapor permeation.

Adhesives useful in the present invention include permanent adhesives, modified polymer adhesives and polymer resins commonly available from many commercial sources. It is contemplated that acrylic and anhydride modified polymers may be employed as well as many adhesives which may be selected depending upon other material selections for other functional layers such as the oxygen and/or moisture barrier layer(s) as well as the exterior abuse resistant or protecting layer as well as the required COC layer.

Additives and processing aides; natural and synthetic colorants, pigments and dyes; fillers such as calcium carbonate or carbon black, antimicrobial agents may be incorporated into or coated on one or more layers of the multilayer films of the present invention.

Film Thickness

Preferably, the packaging film has a total thickness of less than about 10 mils, more preferably the film has a total thickness of from about 1.0 to 10 mils (25-250 microns (μ)). Advantageously many embodiments may have a thickness from about 1 to 5 mils, with certain typical embodiments being from about 2 to 3.5 mils. For example, entire multilayer films or any single layer of a multilayer film can have any suitable thicknesses, including 1, 2, 3, 4, 5, 6, 7, 8, 9, or 10 mils, or any increment of 0.1 or 0.01 mil therebetween. Although suitable films for packaging drug patches as thick as 4 mils (101.6 microns) or higher, or as thin as 1 mil (25.4 microns) or less may be made, it is expected that the most common films will be between about 2-4 mil (51-1 02 microns). Especially preferred for use as films for transdermal patch packaging are films where the multilayer film has a thickness of between about 2 to 3 mils (50.8-76.2 microns). Such films may have good abuse resistance and machinability.

Typical contents for various embodiments of the inventive container may include, for example, transdermal patches, thin strips of dissolvable material for oral administration, as well as articles for collecting or administering a physiologically active substance e.g. a microdiffusion cassette.

Exemplary of commercially available LDPE resin suitable for use in the present invention includes, but are not limited to Equistar 216-000 LDPE resin. Exemplary of commercially available EAA resin for use in the present invention includes, but is not limited to Dupont 3990-L, which is supplied by Dupont de Nemours. Exemplary of commercially available ionomer resin for use in the present invention includes, but is not limited to Dupont 1652-1 Surlyn, which is supplied by Dupont de Nemour. Exemplary of commercially available EAA resin for use in the present invention includes, but is not limited to Dupont 3990-L, which is supplied by Dupont de Nemours.

The mLLDPE layer used in the examples was a blend of 80% LDPE comprising and 20% mLLDPE.

Exemplary of commercially available LDPE resin for use in the present invention includes, but is not limited to Dow 4012 LDPE which is supplied by Dow Chemical Co. of Midland, Mich., USA.

Exemplary of commercially available mLLDPE resin for use in the present invention includes, but is not limited to Exxon Exact 3040 mLLDPE resin, which is supplied by Exxon.

Exemplary of commercially available COC resin for use in the present invention includes, but is not limited to Topas 8007F-400, which is supplied by Topas Advanced Polymers.

The containers e.g. a pouch can further include a tearing aid or tear initiator such as a notch. Examples of tearing aids or tear initiators such as notches, slits, perforations, surface roughened portions, etc., are described in U.S. Pat. Nos. 4,778,058; 3,608,815; 4,834,245; 4,903,841; 5,613,779; 5,988,489; 6,102,571; 6,106,448; 6,541,086; 7,470,062; and 7,481,581. Such tear initiators may be used on one or more edges of the inventive pouch and package.

Advantageously the tear initiator may be used with scoring e.g. mechanical or laser scoring of one or more layers, preferably the other abuse resistance layer, to create a tear directing line which facilitates opening. Prior art films used for packaging transdermal patches which utilize polyacrylonitrile as the patch contact surface layer (sealant layer) have undesirably poor tear properties, being very susceptible to delamination upon attempts to tear open even with scoring. These packages typically must use scissors or a knife for opening. Beneficially, the present invention has excellent tear properties and when used with a score line may be manually opened in a clean, non-delaminating fashion without use of scissors or other cutting implements. This easy to open feature of the present invention may be coupled with child resistant packaging technology such as that described in pending patent application number PCTIUS2013/022101, which is hereby incorporated by reference in its entirety, to provide a child resistant package which is simultaneously easy to open by an adult.

Relationship Between Pharmaceutical Active and Product Contacting Layer

As indicated above, it is proposed herein that both the glass transition temperature of the layer comprising ethylene norbornene copolymer and the Hansen Solubility Parameter (HSP) of the active pharmacological agent to be stored in contact (direct or indirect) with the product contacting layer comprising ethylene norbornene copolymer can be factors in determining whether the product contacting layer can serve as an effective anti-scalping layer.

Based on experiments described herein, we now believe that the HSP provides a thermodynamic indication of whether the active agent will migrate into the product contacting layer, with higher HSPs favoring lower amounts of migration. We also now believe that the glass transition temperature provides a kinetic indication of the rate at which the active agent will migrate into the product contacting layer, with higher glass transition temperatures tending to result in slower kinetics and thus better anti-scalping properties.

In various embodiments, the pharmaceutical active agent has a HSP for the film or layer of 0.5 or greater and has a glass transition temperature of 50° C. or greater. The HSP is preferably 0.6 or greater, such as 0.7 or greater, 0.8 or greater, 0.9 or greater, or 1 or greater. Preferably, the glass transition temperature is 55° C. or greater, such as 60° C. or greater, 65° C. or greater, or 75° C. or greater. In various embodiments, the glass transition temperature is 138° C. or less. Preferably, the glass transition temperature is 110° C. or less. In some embodiments, the glass transition temperature of the product contacting layer is in a range from 50° C. to 138° C., such as in a range from 55° C. to 138° C., in a range from 50° C. to 110° C., in a range from 65° C. to 110° C., or the like.

The HSP of a pharmaceutical active agent for a layer comprising an ethylene norbornene copolymer as described herein can be determined as described in Hansen, C. M., Hansen Solubility Parameters a User's Handbook 2nd Ed., CRC Press, Boca Raton, 2007. According to Hansen, the total cohesion energy (E) of a liquid is defined by the energy required to convert a liquid to a gas. This can be experimentally measured by the heat of vaporization. Hansen described the total cohesion energy as being comprised of three primary intermolecular forces: atomic dispersion forces ($E_D$), molecular permanent dipole-dipole interactions ($E_P$), and molecular hydrogen bonding interactions ($E_H$). When the cohesion energy is divided by the molar volume (V) the total cohesive energy density of the liquid is given by:

$$E/V = E_D/V + E_P/V + E_H/V. \qquad (1)$$

The solubility parameter ($\delta$) of the liquid is related to the cohesive energy density by:

$$\delta = (E/V)^{1/2}. \qquad (2)$$

where $\delta$ is the Hildebrand solubility parameter. The three Hansen solubility components of a liquid are thus given by:

$$\delta^2 = \delta_D^2 + \delta_P^2 + \delta_H^2. \qquad (3)$$

These three parameters have been tabulated for thousands of solvents and can be used to describe polymer-solvent interactions (see, e.g., Hansen, 2007).

Solubility parameters exist for solid polymers as well as liquid solvents (see, e.g., Hansen, 2007). Polymer-solvent interactions are determined by comparing the Hansen solubility parameters of the polymer to that of a solvent or solvent mixture defined by the term $R_a$ as $$R_a^2 = 4(\delta_{D2} - \delta_{D1})^2 + (\delta_{P2} - \delta_{P1})^2 + (\delta_{H2} - \delta_{H1})^2 \qquad (4)$$

where subscripts 1 and 2 refer to the solvent or solvent mixture and polymer respectively. $R_a$ is the distance in three dimensional space between the Hansen solubility parameters of a polymer and that of a solvent. A "good" solvent for a particular polymer has a small value of $R_a$. This means the solubility parameters of the polymer and solvent are closely matched and the solvent will quickly dissolve the polymer. $R_a$ will increase as a solvent's Hansen solubility parameters become more dissimilar to that of the polymer.

The solubility of a particular polymer is not technically described by just the three parameters in Equation (3). A good solvent does not have to have parameters that perfectly match that of the polymer. There is a range of solvents that will work to dissolve the polymer. The Hansen solubility parameters of a polymer are defined by $\delta_D$, $\delta_P$, and $\delta_H$ which are the coordinates of the center of a solubility sphere which has a radius ($R_o$). $R_o$ defines the maximum distance from the center of the sphere that a solvent can be and still dissolve the polymer.

The strength of a solvent for a polymer is determined by comparing $R_a$ to $R_o$. A term called the Relative Energy Difference (RED) is given by:

$$RED = R_a/R_o. \qquad (5)$$

Using RED values is a simple way to evaluate how "good" a solvent or active agent will be for a given polymer. Solvents or active agents that have a RED number much less than 1 will have Hansen solubility parameters close to that of the polymer and will dissolve. Solvents or active agents that have RED numbers much greater than 1 will have Hansen solubility parameters further away from the polymer and will have little or no ability to dissolve polymer. Solvents or active agents that have RED numbers close to one will be on the boundary between good and poor solvents and will partially dissolve.

HSP values provided herein are RED values. RED values for a pharmaceutical active agent and a layer comprising ethylene norbornene copolymer can be determined experimentally or by identifying $R_a$ values in existing databases, such as the HSPiP Datasets available at http://hansen-solubility.com/HSPiPDatasets.html. For polymer blends, $R_a$ values of the various polymers forming the blend can be averaged. If a polymer blend contains 90% or more of one polymer, e.g., at least 90% of an ethylene norbornene copolymer, then, for purposes of the present disclosure, the $R_a$ value for the polymer blend can be assumed to be the $R_a$ value of the polymer making up 90% or more of the blend.

For purposes of the present disclosure, a pharmaceutical composition is considered to be a pharmaceutical "product." Preferably, the RED values of one or more of the excipients for the ethylene norbornene copolymer are 0.5 or greater. More preferably, the RED values are 0.6, 0.7, 0.8, 0.9, or 1 or greater. The RED values for excipients can be obtained generally as described above with regard to the pharmaceutical active agents.

Excipients that may be included in various types of pharmaceutical products are generally known to those of ordinary skill in the pharmaceutical arts and may be provided in Remington: The Science and Practice of Pharmacy, $22^{nd}$ edition, Loyd V. Allen, Jr. (editor), Pharmaceutical Press, September 2012.

A pharmaceutical product for packaging in a film described herein can include any suitable pharmaceutical active agent. In some embodiments, the pharmaceutical active agent is selected from the group consisting of fentanyl, nicotine, lidocaine, estradiol, clonidine, ethinyl estradiol, oxybutynin, buprenorphine, granisitron, methylphenidate, and scopolamine. In some embodiments, one or more of the listed pharmaceutical active agents are included in a transdermal patch.

Examples of some excipients that may be present in a transdermal patch include solvents, preservatives, and permeation enhancers. Examples of some particular excipients include isopropyl myristate, ethyl lactate, lauryl lactate, dimethylsulfoxide (DMSO), capric acid, dipropylene glycol, ethanol, oleic acid, triacetin, isopropyl palmitate, water, tetradecane and the like.

HSP (RED) values of various pharmaceutical active agents and excipients for various sealant film polymers is listed below in Table 1.

TABLE 1

HSP Data Comparing Various Sealant Films

| HSP Data | CXB | Barex | PE | PET | EVOH |
|---|---|---|---|---|---|
| Drugs | | | | | |
| Fentanyl | 0.51 | 1.04 | 2.34 | 0.32 | 1.38 |
| Nicotine | 1.33 | 0.86 | 2.93 | 0.19 | 1.03 |
| Lidocaine | 1.32 | 0.9 | 2.85 | 0.23 | 1.12 |
| Phenylethylamine | 1.03 | 1.14 | 21.4 | 0.28 | 1.31 |
| Estradiol | 1.62 | 0.97 | 3.12 | 0.46 | 0.93 |
| Clonidine | 2.2 | 0.39 | 4.52 | 0.83 | 0/62 |
| Ethinyl Estradiol | 1.38 | 0.92 | 0.37 | 3.01 | 0.98 |
| Oxybutynin | 0.79 | 1.28 | 1.52 | 0.41 | 1.57 |
| Buprenorphine | 1.18 | 1.08 | 2.42 | 0.29 | 1.19 |
| Granisron | 1.74 | 0.63 | 3.8 | 0.61 | 0.98 |
| D Limonene | 0.61 | 1.56 | 0.55 | 0.81 | 2.02 |
| Methylphenidate | 0.71 | 1.2 | 1.79 | 0.35 | 1.47 |
| Scopalamine | 1.65 | 0.97 | 3.01 | 0.35 | 0.97 |
| Excipients | | | | | |
| Isopropyl Myristate | 0.83 | 1.63 | 0.41 | 0.91 | 2.14 |
| Ethyl Lactate | 2.7 | 1.21 | 4.22 | 1.06 | 1.18 |
| Lauryl Lactate | 1.23 | 1.36 | 1.7 | 0.55 | 1.61 |
| Dimethylsulfoxide | 3.15 | 0.65 | 5.6 | 1.33 | 1.03 |
| Capric Acid | 1.47 | 1.37 | 2.01 | 0.61 | 1.57 |
| Dipropylene Glycol | 3.38 | 1.23 | 1.44 | 5.35 | 1.23 |
| Ethanol | 3.77 | 1.52 | 1.73 | 5.76 | 1.63 |
| Oleic Acid | 0.6 | 1.42 | 0.6 | 1.2 | 1.75 |
| Oleyl Alcohol | 1.31 | 1.45 | 0.67 | 1.62 | 1.7 |
| Triacetin | 1.59 | 1.17 | 2.56 | 0.47 | 1.28 |
| Isopropyl Palmitate | 0.86 | 1.64 | 0.45 | 0.93 | 2.16 |
| Water | 8.53 | 3.26 | 13.23 | 4.67 | 4.4 |
| Tetradecane (C14H30) | 1.02 | 1.84 | 0.92 | 1.25 | 2.51 |

In Table 1, CXB is an ethylene norbornene copolymer from 35 wt. % ethylene monomers and 65 wt. % norbornene monomers; PE is a polyethylene homopolymer; PET is poly(ethylene terephthalate); and EVOH is an ethylene vinyl alcohol copolymer formed from 24 to 48 wt. % ethylene.

As shown in Table 1, all of the listed drugs (active agents) and excipients have a HSP for CXB of greater than 0.5. All of the listed drugs and excipients, except for fentanyl, have a HSP for CXB of 0.6 or greater. All of the listed drugs and excipients, except for fentanyl, D-limonene and oleic acid, have a HSP for CXB of 0.7 or greater. All of the listed drugs and excipients, except for fentalyl, D-limonene, oleic acid, methylphenidate and oxybutynin have a HSP for CXB of 0.8 or greater. All of the listed drugs and excipients, except for fentalyl, D-limonene, oleic acid, methylphenidate, oxybutynin, isopropyl myristate and isopropyl palmitate, have a HSP for CXB of 0.9 or greater. The remaining drugs and excipients have HSPs for CXB or 1 or greater.

A pharmaceutical product can be packaged in a film described herein in any suitable manner. In some embodiments, a pharmaceutical product is packaged such that the pharmaceutical active agent is not in contact with a sealing layer of the film. In some embodiments, the pharmaceutical product is packaged such that the pharmaceutical active agent is in contact with the sealing layer of the film. The active agent can be in direct contact with the sealing layer or in indirect contact with the sealing layer.

In some embodiments, the pharmaceutical product comprises a gel, paste, solution or the like, where gel, paste, solution, etc. contains the active ingredient and is in direct contact with the sealing layer.

In some embodiments, the pharmaceutical product includes an active agent or excipient that acts as a carrier for the active agent where the active agent or the carrier have a vapor pressure sufficiently high to cause volatilization of the active agent or carrier to cause the active agent to contact the sealing layer upon storage, even though the product is initially packaged such that active agent is not in direct contact with the sealing layer.

In some embodiments, the pharmaceutical product includes a transdermal patch. Transdermal patches typically have a release liner covering a matrix comprising a pharmaceutical active agent. Accordingly, the pharmaceutical active agent and excipients of a transdermal patch having a release liner may not be in direct contact with the sealing layer of film in which it is packaged. However, at an edge of the release liner, some of the matrix may come into direct contact with the sealing layer and may allow the active agent to be wicked towards the sealing layer. Alternatively or in addition, the vapor pressure of the active agent or a carrier excipient may be sufficiently high to cause the active agent to contact the sealing layer upon storage. By way of example, nicotine, which is often included in transdermal patches, is fairly volatile and has a vapor pressure of 5.65 Pa at 25° C.

In some embodiments, the pharmaceutical product is packaged in a film described herein such that the pharmaceutical active agent is not in contact with the sealant layer. For example, the active agent may be surrounded by a backing and a release liner or may be otherwise contained such that active agent is not in contact with the sealing layer. In such cases, it can still be desirable to have a sealing layer that would be anti-scalping if the active agent were to come into contact with the sealing layer. For example, if the pharmaceutical product includes a release liner configured to prevent contact of the active agent with the sealing layer, the release liner may slip or otherwise partially release during packaging, shipping, storage or the like to expose the active agent to the sealing layer. Even in there is little or no risk that the active agent may be exposed to the sealing layer, it may be desirable for the sealing layer to be anti-scalping for purposes of caution, reassurance, or the like.

When a pharmaceutical product is packaged in a film such that the product contacting sealing layer of the film is in indirect contact with a pharmaceutical active agent of the product, detectable amounts of the pharmaceutical agent are present at a surface of the product contacting layer or migrate into the product contacting layer upon storage of the product in the packaging film. Any suitable technique can be employed to determine whether a pharmaceutical agent of a pharmaceutical product indirectly contacts a layer of a package in which the produce is sealed. That is, if a detectable amount of the agent is present at a surface of a layer or in a layer of the film, then the pharmaceutical agent is "in contact" with the layer of the film for purposes of the present disclosure. Examples of suitable techniques that can be employed to determine whether a pharmaceutical agent of a pharmaceutical product indirectly contacts a layer of a package in which the produce is sealed include Raman spectroscopy, gas chromatography, gas chromatography-mass spectrometry (GCMS), liquid chromatography-mass spectrometry (LCMS), high performance liquid chromatography (HPLC) and the like.

To determine whether a pharmaceutical active agent of a pharmaceutical product is in indirect contact with a sealing layer of a film, the presence of the active agent at or in a sealing layer of the film can be evaluated after the pharmaceutical product has been packaged in the film under storage conditions for an amount of time. The storage conditions and time can be standard storage conditions. The standard storage conditions can be accelerated storage conditions; e.g. at temperatures above room temperature. For examples, the storage conditions can be 20% relative humidity and a temperature of 100° F. for 1, 7, 15 or 31 days.

Alternatively or in addition, to determine whether a pharmaceutical active agent of a pharmaceutical product would be in indirect contact with a sealing layer of a film described herein, the presence of the active agent at or in a surrogate sealing layer of the film can be evaluated after the pharmaceutical product has been packaged in the surrogate film under standard storage conditions for a standard amount of time. Preferably, the surrogate film is not anti-scalping or is not as anti-scalping as a film as described herein. The product can be packaged and stored in the film containing the surrogate sealing layer in a manner similar to how the pharmaceutical product packaged in a film as described herein would be packaged and stored. If the active agent migrates into the surrogate sealing layer, then the active agent can be considered to be "in contact" with the surrogate layer and would be considered to be "in contact" with a sealing layer of any film in which it was stored, such as a film as described herein.

Anti-Scalping

Whether a product contacting layer of a film performs effectively as an anti-scalping layer can be a subjective determination, with differing amounts of migration of a pharmaceutical active agent into a layer of a film being considered acceptable depending on, among other things, the active agent, the amount that the active agent migrates into layers of other films, and the like.

For purposes of the present application, a product contacting layer of a film is considered to serve as an effective anti-scalping layer if (i) a lower amount of the active agent migrates into the product contacting layer of the film (the test film) than migrates into a substantially similar film having a PE, such as a linear low density polyethylene homopolymer, product contacting layer (the reference film) when a product containing the pharmaceutical active agent is positioned relative to the test and reference films such that the pharmaceutical active agent is in direct contact with the product contacting layers of the test and reference films; or (ii) an amount of the active agent migrates into the product contacting layer of the film (the test film) is not more than 15% greater than migrates into a substantially similar film having a Barex® product contacting layer (the reference film) when a product containing the pharmaceutical active agent is positioned relative to the test and reference films such that the pharmaceutical active agent is in direct contact with the prodcut contacting layers of the test and reference films. Preferably, the product is sealed in a cavity formed, at least in part, by the test film and the product is sealed in a cavity formed, at least in part, by the reference film. The sealed product can be stored under identical conditions prior to testing to determine whether less active agent has migrated into the product contacting layer of the test film than the reference film. The storage conditions may be accelerated storage conditions as described above.

Any suitable technique may be employed to determine whether to determine whether less active agent has migrated into the product contacting layer of the test film than the reference film. For example, Raman spectroscopy or gas chromatography, can be used.

In some embodiments, the amount of an active pharmaceutical agent that migrates into a film having a linear low density polyethylene homopolymer as a product contacting layer (as described above) will be 1.5 times of more than the amount of the pharmaceutical active agent that migrates into an anti-scalping product contact layer of a film as described herein. In some embodiments, the amount of an active pharmaceutical agent that migrates into a film having a linear low density polyethylene homopolymer as a product contacting layer (as described above) will be 2 times of more, 3 times or more, or 4 times or more, or 5 times or more than the amount of the pharmaceutical active agent that migrates into an anti-scalping product contact layer of a film as described herein.

In preferred embodiments, an amount of an active pharmaceutical agent that migrates into a film having an ethylene norbornene copolymer as described herein as a sealing layer will be no more than 10% more than the amount of the pharmaceutical active agent that migrates into film having Barex® as a sealing layer. More preferably, the amount of an active pharmaceutical agent that migrates into a film having an ethylene norbornene copolymer as described herein as a sealing layer will be no more than 9% (no more than 8%, no more than 7%, no more than 6%, no more than 5%, no more than 4%, no more than 3%, no more than 2%, or no more than 1%) more than the amount of the pharmaceutical active agent that migrates into film having Barex® as a sealing layer.

A preferred method for determining whether a film is anti-scalping is to compare active agent uptake relative to a linear low density polyethylene homopolymer or Barex® as described above. In preferred embodiments a drug take test is performed generally as follows:

Ten pouches are made with each test film by heat sealing together two pieces of the sample film each measuring 3×3.5 inches on three sides with the same article contact surface facing each other. Next, a standard amount of the drug being tested is placed on a 1×1.25 inch piece of blotter paper and the blotter paper is placed inside the pouch which is then heat sealed.

The pouches are stored at 100° F. and 20% RH and three pouches of each film structure are tested at reported intervals e.g. days 1, 7, 15 and 31. After the allotted time, three pouches are opened by cutting an end seal, and the blotters removed. The blotterless pouches are rinsed with distilled water to remove any drug residue that might be present on the surface of the sealant and excess water is removed from the pouches by shaking. Next, 5 ml of isopropanol spiked with an internal standard (propylene glycol n-propyl ether) is placed in each pouch which is then resealed with heat seals. The resealed pouches are placed on a shaker table for 90 minutes to facilitate drug extraction from the sealant. Finally, the pouch extracts are analyzed by gas chromatography and the amount of eluted drug is calculated for each pouch.

Figures

Referring now to the Drawings, FIG. 1 is a schematic drawing of a cross-section of a multilayer film 10 in accordance with an embodiment described herein. In the depicted embodiment, the film 10 includes six layers. On one surface is the product contacting layer 1, which comprises an ethylene norbornene copolymer. Adjacent and in contact with the product contacting layer 1 is a poleolefin bulk layer 2. Adjacent and in contact with the polyolefin bulk layer 2 is a first intermediate adhesive layer 3. Adjacent and in contact with the first intermediate adhesive layer 3 is an oxygen barrier layer 4. Adjacent and in contact with the oxygen barrier layer 4 is a second intermediate adhesive layer 5. Adjacent and in contact with the second intermediate adhesive layer 5 is an exterior protective layer 6. It will be understood that a film as described herein may have any number of one or more layers and that the six-layered film depicted in FIG. 1 is shown for purposes of example. In some embodiments, a polyolefin bulk layer can serve as an adhesive or tie layer.

Figure 2:
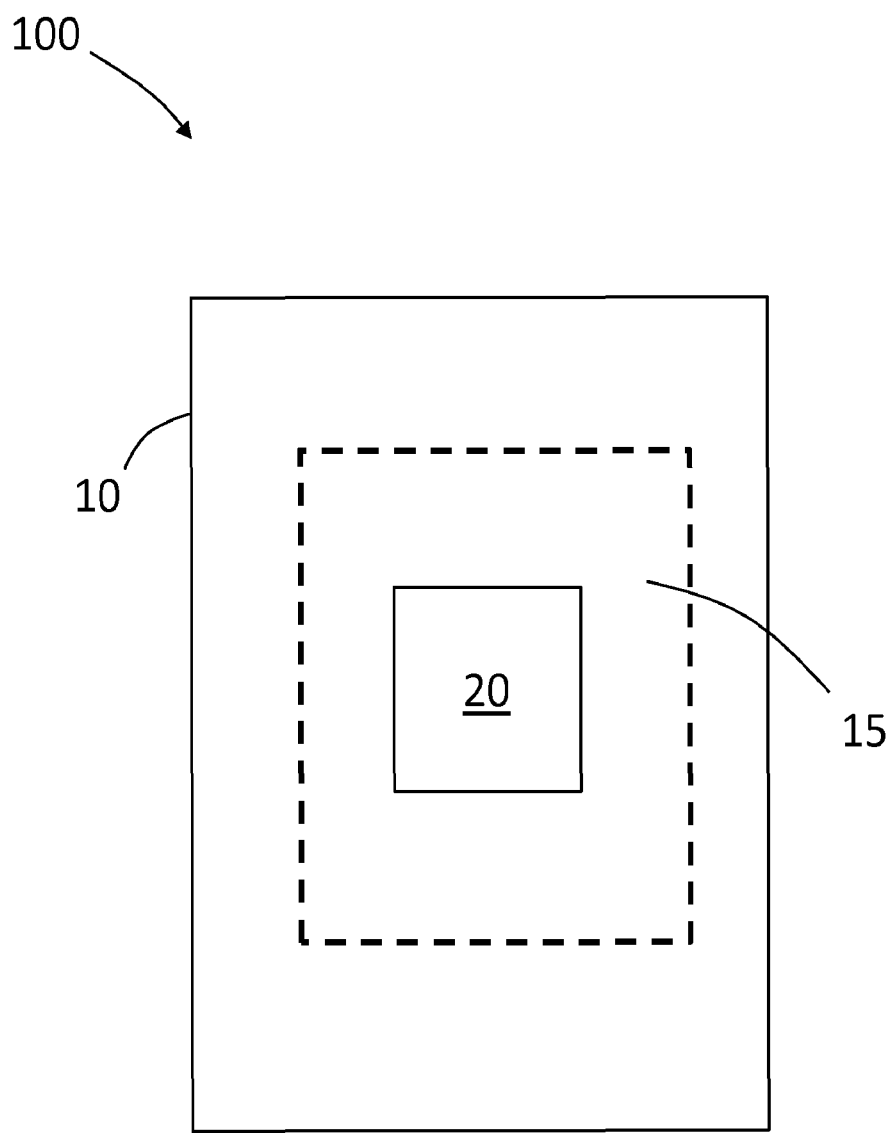
FIG. 2 is a schematic view of a packaged pharmaceutical product in accordance with embodiments presented herein.

Referring now to FIG. 2, a schematic view of a packaged pharmaceutical product 100 is shown. In the depicted embodiment, the packaged pharmaceutical product includes a pharmaceutical product 20 sealed in a packaging film 10 as described herein. The dashed lines in FIG. 2 represent the boundaries of a sealed interior volume 15 formed by the film 10 (in this case, wrapped around the product 20 and sealed).

In some embodiments, a single roll web of pouch film can be placed on a packaging machine and folded together and heat sealed and severed to form heat sealed pouches. Two side sealed pouches with a folded third side can be used to package an article by a manufacturer or packager who places a product in the pouch, and completes the final seal to produce a hermetically sealed package containing for example: a transdermal drug delivery patch; an oral dissolvable thin strip containing a drug, flavorant, antimicrobial agent, odorant, and/or microbiologically active ingredient or combination thereof; or an article for collecting or administering a physiologically active substance.

Experimental results and reported properties are based on the following test methods or substantially similar test methods unless noted otherwise.

Oxygen Gas Transmission Rate (0 2GTR): ASTM D-3985-81
Water Vapor Transmission Rate (WVTR): ASTM F 1249-90
Gauge: ASTM D-21 03
Melt Index (M.I.): ASTM D-1238, Condition E (190° C.) (except for propene-based (>50% $C_3$ content) polymers tested at Condition TL (230° C.))
Melting point: ASTM D-3418, DSC with 5° C./min heating rate
Glass transition temperature Tg ASTM D3418
Gloss: ASTM D-2457, 45° angle Nicotine Direct Contact Test Ten pouches are made with each test film by heat sealing together two pieces of the sample film each measuring 3×3.5 inches on three sides with the same article contact surface facing each other. Next, 50 µl of pure nicotine is placed on a 1×1.25 inch piece of blotter paper and the blotter paper is placed inside the pouch which is then heat sealed.

The pouches are stored at 100° F. and 20% RH and two pouches of each film structure are tested at reported intervals e.g. days 1, 2, 8, 15 and 31. After the allotted time, two pouches are opened by cutting an end seal, and the blotters removed. The blotterless pouches are rinsed with distilled water to remove any liquid nicotine that might be present on the surface of the sealant and excess water is removed from the pouches by shaking. Next, 5 ml of isopropanol spiked with an internal standard (propylene glycol n-propyl ether) is placed in each pouch which is then resealed with heat seals. The resealed pouches are placed on a shaker table for 90 minutes to facilitate nicotine extraction from the sealant. Finally, the pouch extracts are analyzed by gas chromatography and the amount of eluted nicotine is calculated for each pouch.

Nicotine Vapor Test

Ten pouches are made with each test film by heat sealing together two pieces of the sample film each measuring 3×3.5 inches on three sides with the same article contact surface facing each other. Next, 50 µl of pure nicotine is placed on a 1×1.25 inch piece of blotter paper. The blotter paper is then wrapped in perforated foil having approximately 20 needle perforations per side. The foil wrapped blotter paper is placed inside the pouch which is then hermetically sealed. The perforated foil wrapper prevents direct contact of the blotter absorbed nicotine with the sealant layer of the film.

The blotter containing pouches are stored at 100° F. and 20% Relative Humidity (RH). Two pouches of each film structure are tested at recorded intervals e.g. days 1, 2, 8, 15 and 31 as follows. After the allotted time, two pouches are opened by cutting an end seal, and the foil covered blotters are removed. Next, 5 ml of isopropanol, spiked with an internal standard (propylene glycol n-propyl ether), is placed in each pouch and each blotterless pouch is resealed with heat seals. The resealed pouches are then placed on a shaker table for 90 minutes to facilitate nicotine extraction from the sealant. Finally, the pouch extracts are analyzed by gas chromatography and the amount of eluted nicotine is calculated for each pouch.

Eluted nicotine values are measured by the methods described above or tests similar thereto, unless otherwise specified.

Drug Uptake Test

Ten pouches are made with each test film by heat sealing together two pieces of the sample film each measuring 3×3.5 inches on three sides with the same article contact surface facing each other. Next, a standard amount of the drug being tested is placed on a 1×1.25 inch piece of blotter paper and the blotter paper is placed inside the pouch which is then heat sealed.

The pouches are stored at 100° F. and 20% RH and three pouches of each film structure are tested at reported intervals e.g. days 1, 7, 15 and 31. After the allotted time, three pouches are opened by cutting an end seal, and the blotters removed. The blotterless pouches are rinsed with distilled water to remove any drug residue that might be present on the surface of the sealant and excess water is removed from the pouches by shaking. Next, 5 ml of isopropanol spiked with an internal standard (propylene glycol n-propyl ether) is placed in each pouch which is then resealed with heat seals. The resealed pouches are placed on a shaker table for 90 minutes to facilitate drug extraction from the sealant. Finally, the pouch extracts are analyzed by gas chromatography and the amount of eluted drug is calculated for each pouch.

Drug Vapor Test

Ten pouches are made with each test film by heat sealing together two pieces of the sample film each measuring 3×3.5 inches on three sides with the same article contact surface facing each other. Next, a standard amount of the drug being tested is placed on a 1×1.25 inch piece of blotter paper. The blotter paper is then wrapped in perforated foil having approximately 20 needle perforations per side. The foil wrapped blotter paper is placed inside the pouch which is then hermetically sealed. The perforated foil wrapper prevents direct contact of the blotter absorbed drug with the sealant layer of the film.

The blotter containing pouches are stored at 100° F. and 20% Relative Humidity (RH). Three pouches of each film structure are tested at recorded intervals e.g. days 1, 7, 15 and 31 as follows. After the allotted time, three pouches are opened by cutting an end seal, and the foil covered blotters are removed. Next, 5 ml of isopropanol, spiked with an internal standard (propylene glycol n-propyl ether), is placed in each pouch and each blotterless pouch is resealed with heat seals. The resealed pouches are then placed on a shaker table for 90 minutes to facilitate drug extraction from the sealant. Finally, the pouch extracts are analyzed by gas chromatography and the amount of eluted drug is calculated for each pouch.

Eluted drug values are measured by the methods described above or tests similar thereto, unless otherwise specified.

Raman Spectroscopy

For purposes of illustration, a Raman Spectroscopy method for samples in direct contact with a nicotine composition is now described. One will understand that the method can be readily modified for use with indirect drug contact or for use with other drugs.

Film Samples in direct contact with nicotine for a specified time were analyzed using a Confocal Raman microscope (Thermo Fisher DXRxi) using a 100× (numerical aperture: 0.90) objective, a laser wavelength of 532 nm (10 mW of power at sampling point) and an exposure time of 0.04 seconds per spectrum. The estimated spot size on the sample was 0.2 μm and the confocal aperture used was 25 μm. Spectra between wavenumbers 500-3500 $cm^{-1}$ were collected. Spectra were collected in the form of a depth profile from a section of the film (100×100 μm) with a Raman image pixel size specified as 2 um and the total number of scans was 10. As a result, each Raman image is a composite of results from 25,000 spectra. The Raman image was generated using proprietary software (Thermo Fisher Scientific) included with the Raman microscope used. Area under the peaks (wavenumber range: 1004-1064 $cm^{-1}$) was used to indicate relative nicotine concentration at each point on the generated Raman image on a rainbow scale (low: blue, high: red). Pure nicotine liquid has peaks at 1026 $cm^{-1}$ and 1042 $cm^{-1}$.

Following are examples given to illustrate the invention, but these examples should not be taken as limiting the scope. All percentages are by weight unless indicated otherwise.

Films of 6, 7, 8, 9 or more layers are contemplated. The inventive multilayer films may include additional layers or polymers to add or modify various properties of the desired film such as heat sealability, interlayer adhesion, wrinkle resistance, puncture resistance, printability, toughness, gas and/or water barrier properties, abrasion resistance, printability, and optical properties such as gloss, haze, freedom from lines, streaks or gels. These layers may be formed by any suitable method including coextrusion, extrusion coating and lamination.

Unless otherwise noted, the thermoplastic resins utilized in the present invention are generally commercially available in pellet form and, as generally recognized in the art, may be melt blended or mechanically mixed by well-known methods using commercially available equipment including tumblers, mixers or blenders. Also, if desired, well known additives such as processing aids, slip agents, anti-blocking agents and pigments, and mixtures thereof may be incorporated into the film or applied to one or more surfaces thereof, e.g. by blending prior to extrusion, powdering, spraying, contact roller application, etc. Typically the resins and any desired additives are mixed and introduced to an extruder where the resins are melt plastified by heating and then transferred to an extrusion (or coextrusion) die. Extruder and die temperatures will generally depend upon the particular resin or resin containing mixtures being processed and suitable temperature ranges for commercially available resins are generally known in the art, or are provided in technical bulletins made available by resin manufacturers. Processing temperatures may vary depending upon other processing parameters chosen.

Examples 1-5

Examples 1-4 are comparative examples (not of the invention). Example 5 is an example according to the present invention. In all of the examples, a multilayer film is provided having a base film and connected sealant film. The sealant film has a surface layer which is designed to contact the article to be packaged e.g. a transdermal patch article, and to permit heat sealing of the multilayer film to form a container such as a pouch. The EAAlLDPE/COC sealant layer of the invention and the comparative sealant layers were either extrusion coated or adhesively laminated. In all of the examples 1-5, a multilayer base film having the following structure: OPET/Primer/PE/EAA/Foil was made and only the connected sealant film was varied.

Base Film

The base film was comprised of five layers having an ordered structure of:

/Layer 11 Layer 2/Layer 3/Layer 4/Layer 5/corresponding to:

/exterior layer 11 primer layer 2/bulk layer 3/adhesive layer 4/0 2layer 5/; or more particularly, /OPET/PEI/LDPE/EVA/Al Foil/.

Layer 1 was a commercially available 0.92 mil, biaxially oriented polyethylene terephthalate (OPET) film corona treated on one side. The treated OPET film received a second corona treatment on the previously treated side prior to receiving an anchor coating of a water-based polyethyleneimine (PEI) primer (Layer 2) that was contact coated onto the corona treated side of the OPET film and dried just prior to lamination of the OPET film to 0.35 mil aluminum foil (Layer 5) using a coextrusion of LDPE (Layer 3) and EAA (Layer 4). Layers 3 and 4 were produced by the two-layer coextrusion of LDPE and EAA. The anchor coated side of the OPET film was laminated to 0.35 mil aluminum foil with a coextrusion of LDPE and EAA. The LDPE was a blend of 87.5 wt. % LDPE laminate resin and 12.5 wt. % of a white colorant in a carrier resin. The oxygen and moisture barrier was provided by a commercially available aluminum foil.

Comparative Example 1

In example 1, a sealant film of ionomer was extrusion coated onto a five layer base film made as described above. The aluminum foil surface of the multilayer base film having the structure OPET/primer/LDPE/EAA/foil was corona treated and then extrusion coated with ionomer. The ionomer used was a zinc salt of ethylene-methacrylate acid copolymer commercially available under the trademark Surlyn® 1652-1 and having a reported density of 0.940 $g/cm^3$ and meh index of 4.5 g/10 min.

The resultant six layer, multilayer film had the following structure: 0.92 mil OPET/primer/coex (0.42 mil LDPE/0.1 mil EAA)/0.35 mil foil 1.0 mil ionomer, and had a total nominal thickness of 2.8 mils (71 microns).

Comparative Example 2

The base film for example 2 was produced in the same manner as for example 1 except that the aluminum foil was not corona treated prior to the addition of the sealant film. In comparative example 2, a three-layer coextrusion of: EAA; LDPE; and an 80:20 wt % blend of LDPE:mLLDPE was extrusion coated onto the aluminum foil surface of the multilayer base film with the EAA layer adhered to and in direct contact with the aluminum foil. The resultant multilayer film had the following structure 0.92 mil OPET/primer/(0.42 mil LDPE/0.1 mil EAA)/0.35 mil foil/0.17 mil EAA/0.65 mil LDPEI 0.43 mil LDPE:mLLDPE and a total thickness of 3.04 mils (77.2 microns).

Comparative Example 3

The base film for example 3 was produced in the same manner as for example 2. In comparative example 3, the sealant film was a commercially available, corona treated, cast APET film. The APET film received an additional corona treatment prior to adhesive lamination. The base and sealant films were laminated by coating the aluminum foil surface of the multilayer base film having the structure OPET/primer/LDPE/EAA/foil with a 2-part urethane adhesive using an analox roller followed by laminating contact to a corona retreated cast APET film. The resultant 7 layer film had the following structure: 0.92 mil OPET/primer/0.42 mil LDPE/0.1 mil EAA)/0.35 mil foil/0.08 mil adhesive/2 mil APET (inside) and a total thickness of 3.9 mils (99 microns).

Comparative Example 4

The base film for example 4 was produced in the same manner as for example 2 except that the LDPE/EAA coextrusion was applied slightly thicker. In comparative example 4, the sealant film was a corona treated polyacrylonitrile film. The polyacrylonitrile film received an additional corona treatment just prior to lamination. The aluminum foil surface of the multilayer base film having the structure OPETiprimer/LDPE/EAA/foil was then coated with a 2-part urethane adhesive using an analox roller and the structure was adhesively laminated to the corona retreated polyacrylonitrile film. The resultant multilayer film had the following structure (outside) 0.92 mil OPET/primer/0.56 mil LDPE/0.1 mil EAA)/0.35 mil foil/0.07 mil Adhesive/1.5 mil Barex (inside) and a total thickness of 3.5 mil.

Example 5 (of the Invention)

The film structure in Example 5 is exemplary of a film according to the present invention. The base film for example 5 was produced in the same manner as for comparative example 2. In this example, the sealant film was a three-layer coextrusion of EAA, LDPE and Ethylene-norbornene copolymer (COC) which was extrusion coated onto the aluminum foil surface of the multilayer base film to produce an eight layer film having the structure: 0.92 mil OPET/primerl0.42 mil LDPEI0.1 mil EAN0.35 mil foill0.17 mil EAA/0.65 mil LD/PE/0.43 mil COC and a total thickness of 3.0 mils (76 microns). The inventive film is well suited to package articles for collecting or administering a physiologically active substance such as transdermal drug delivery patches, or oral dissolvable thin strips and has advantageous moisture barrier, oxygen barrier, and low scalping properties as discussed below. The resultant multilayer film was tested for various properties which are reported below.

Scalping Tests for Examples 1-5

Each of the films made in Examples 1-5 were tested for nicotine scalping by a "Nicotine Direct Contact Test" and a "Nicotine Vapor Test". Properties are reported in Table 2 below.

TABLE 2

| Ex. No. | Sealant Layer | Ave. Sealant Thickness (mil) | Nicotine Direct Contact Test Amount of Eluted Nicotine (mg) | | | | | Nicotine Vapor Test Amount of Eluted Nicotine (mg) | | | | |
|---|---|---|---|---|---|---|---|---|---|---|---|---|
| | | | Day 1 | Day 2 | Day 8 | Day 15 | Day 31 | Day 1 | Day 2 | Day 8 | Day 15 | Day 31 |
| 1 | Ionomer | 1.0 | 17.1 | 15.3 | 16.7 | 24.0 | 22.0 | 8.5 | 11.9 | 15.8 | 25.2 | 23.7 |
| 2 | LDPE:mLLDPE 80:20 wt. % blend | 0.43 | 10.5 | 10.8 | 13.3 | 17.0 | 15.8 | 5.76 | 7.85 | 11.5 | 17.2 | 16.2 |
| 3 | APET | 2 | 12.6 | 10.5 | 12.0 | 13.1 | 11.2 | 1.73 | 2.47 | Leak in Pouch | Leak in Pouch | 2.3 |
| 4 | polyacrylonitrile | 1.5 | 0.05 | 0.00 | 0.00 | 0.03 | 0.03 | 0.21 | 0.36 | 0.49 | 0.70 | 1.08 |
| 5 | COC | 0.43 | 2.08 | 3.47 | 1.42 | 3.12 | 2.03 | 0.94 | 1.26 | 1.95 | 2.42 | 1.26 |

Example 6—Testing of Additional Agents

Tested Structures:
APET: 92 ga OPET/7.5# White PE Coex/35 ga Foil/1.7# Adh./2 mil APET (35680-G)
CXB™: 92 ga OPET/9.6# White PE Coex/35 ga Foil/1.7# Adh./2 mil CXB (LLDPE-COC) (35694-G)
Barex®: 92 ga OPET/9.6# White PE Coex/35 ga Foil/1.7# Adh./2 mil Barex® (35434-G)
PE: 48 ga OPET/9.6# White PE Coex/35 ga Foil/1.7# Adh./2 mil EVA (5% VA) (35775-G)
92 ga OPET/7.5# White PE Coex/35 ga Foil/18# EAA/LDPE (35417)
Ionomer: 48 ga OPET/9.3# White PE Coex/28.5 ga Foil/15# Ionomer (35698)

When choosing testing materials, PE based sealants were chosen as a negative control and Barex® was chosen as a positive control. The goal of an anti-scalping sealant is to perform better than PE and show close (if not matched) performance to Barex®

With Barex® being the gold standard for uptake, a goal of at least 85% of Barex® performance was set. Though each application will differ in barrier requirements, those that do require minimal uptake and are currently are in Barex® will require performance close to that of Barex® to minimize packaging risk.

In the case of Nicotine uptake testing, CXB™ performed at 95.2% Barex® performance with direct contact and 98% Barex® performance with indirect contact. In subsequent nicotine uptake studies, CXB™ had greater than 98% of Barex® performance Estradiol Uptake, and HSP
Direct Contact

| day | Ionomer | Barex | APET | 35775-PE | CXB |
|---|---|---|---|---|---|
| 1 | 0.0000 | 0.0000 | 0.0000 | 0.0000 | 0.0000 |
| 7 | 0.0000 | 0.0000 | 0.0000 | 0.0000 | 0.0000 |
| 18 | 0.0073 | 0.0000 | 0.0000 | 0.0048 | 0.0055 |
| 30 | 0.0051 | 0.0000 | 0.0137 | 0.0000 | 0.0088 |
| 60 | 0.0029 | 0.0000 | 0.0161 | 0.0058 | 0.0132 |

Very small amounts of estradiol can be detected in several of the samples. It is unclear at this point if the values are indicative of an accurate trend of uptake.

Indirect Contact (Vapor Contact)

| day | Ionomer | Barex | APET | 35775-PE | CXB |
| --- | --- | --- | --- | --- | --- |
| 1 | 0.00000 | 0.00000 | 0.00000 | 0.00000 | 0.00000 |
| 7 | 0.00000 | 0.00000 | 0.00000 | 0.00000 | 0.00000 |
| 18 | 0.00065 | 0.00000 | 0.00000 | 0.00000 | 0.00000 |
| 30 | 0.00000 | 0.00000 | 0.00000 | 0.00000 | 0.00000 |
| 60 | 0.00000 | 0.00000 | 0.00296 | 0.01614 | 0.00000 |

In the indirect uptake test, PE and APET show detectable amounts of Estradiol while the other materials show no uptake. The estradiol values in this case remain very low.

HSP: (no RED value for Ionomer)

| RED Values | CXB | Barex | PE (low Tg) | PET |
| --- | --- | --- | --- | --- |
| Estradiol | 1.62 | 0.97 | 3.12 | 0.46 |

Raman: No penetration of Estradiol could be detected with Raman Spectroscopy in the uptake samples.

Lidocaine Uptake, HSP, and Raman
Direct Contact

| Direct Contact (avg mg of Lidocaine) | | | | | |
| --- | --- | --- | --- | --- | --- |
| day | Ionomer | Barex | APET | 35775-PE | CXB |
| 0 | 0.0000 | 0.0000 | 0.0000 | 0.0000 | 0.0000 |
| 1 | 0.3283 | 0.0467 | 0.0693 | 0.1559 | 0.0124 |
| 7 | 1.8896 | 0.1055 | 0.2392 | 0.5739 | 0.0214 |
| 18 | 1.9872 | 0.5642 | 0.3339 | 0.6513 | 0.0473 |
| 30 | 2.7984 | 0.1328 | 0.6924 | 0.8306 | 0.1347 |
| 60 | 2.85 | 0.43 | 1.19 | 0.72 | 0.25 |

Direct contact shows CXB as the best performance, even exceeding the performance of Barex®.

Indirect Contact (Vapor Contact)

| Vapor Contact (avg mg of Lidocaine) | | | | | |
| --- | --- | --- | --- | --- | --- |
| day | Ionomer | Barex | APET | 35775-PE | CXB |
| 0 | 0.0000 | 0.0000 | 0.0000 | 0.0000 | 0.0000 |
| 1 | 0.0125 | 0.0090 | 0.0083 | 0.0137 | 0.0055 |
| 7 | 0.0400 | 0.0199 | 0.0194 | 0.0276 | 0.0075 |
| 14 | 0.0492 | 0.0352 | 0.0272 | 0.0536 | 0.0107 |
| 30 | 0.0664 | 0.0719 | 0.0506 | 0.0809 | 0.0209 |
| 60 | 0.3570 | 0.2999 | 0.1717 | 0.2452 | 0.1389 |

Again with vapor contact, CXB™ is the best performer.

HSP:

| RED Values | CXB | Barex | PE (low Tg) | PET |
| --- | --- | --- | --- | --- |
| Lidocaine | 1.32 | 0.9 | 2.85 | 0.23 |

Raman: Permeation of Lidocaine could only be seen in Ionomer and PE after 28 days of direct contact. PE permeation resulted in the Lidocaine diffusing all the way through the sealant layer and settling at the sealant/foil interface.

Based on the results of the above examples, the inventors now believe that two factors play a role in permeation characteristics; namely, thermodynamic and kinetic interactions. Again, based on the results presented herein, the inventors believe that both of these interactions will, together, provide a more full understanding of the permeation properties of a sealant film relative to either factor in isolation. Thermodynamic interactions can be predicted through solubility modeling. Kinetic interactions are based on the structure of the polymer and the molecular weight of the active agent in the product. Assuming all transdermal drugs are low molecular weight, the polymer characteristics can be used to predict the kinetic interaction. In this case, Tg can be used as a factor for determining the rate at which a drug will diffuse through a polymer, with a higher Tg resulting in a lower diffusion rate. However, the Tg should be low enough to allow the polymer to be heat sealable. Thus the HSP RED value can be factored in, with higher RED values indicating lower solubilities (thermodynamic factor). The more soluble the drug is in the sealant, the more permeation will occur. Low permeation anti-scalping heat sealable films or layers can be obtained by balancing RED (thermodynamic) and Tg (kinetic factors).

Based on the results presented herein, the inventors believe that flms or layers comprising 90% or more of an ethylene norbornene copolymer and having a glass transition temperature of 50-138° C., an ethylene-norbornene comonomer content of 20-40 mole % ethylene and 30-60 mole % norbornene, or a glass transition temperature of 50-138° C. and an ethylene-norbornene comonomer content of 20-40 mole % ethylene and 30-60 mole % norbornene can provide a heat-sealable film or layer that is anti-scalping with respect to a number of active pharmaceutical agents, particularly those having HPS RED values of 0.5 or greater, such as 0.6 or greater, 0.7 or greater, 0.8 or greater, 0.9 or greater, or 1 or greater.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:

1. A film for packaging a product comprising a pharmaceutical active agent, the film comprising:
    a product-contacting sealing layer comprising at least 90 wt. % of an ethylene norbornene copolymer having a glass transition temperature in a range from 50° C. to 110° C.;
    wherein the pharmaceutical active agent comprises one or more of fentanyl, nicotine, estradiol, clonidine, ethinyl estradiol, oxybutynin, buprenorphine, granisitron, methylphenidate, and scopolamine; and
    wherein the pharmaceutical active agent comprises a Hansen Solubility Parameter for the product-containing sealing layer of 0.5 or greater.

2. A film according to claim 1, wherein the pharmaceutical active agent comprises a Hansen Solubility Parameter for the polymeric sealing layer of 0.7 or greater.

3. A film according to claim 1, wherein the pharmaceutical active agent comprises a Hansen Solubility Parameter for the polymeric sealing layer of 1 or greater.

4. A film according to claim 1, wherein the sealing layer consists essentially of ethylene norbornene copolymer.

5. A film according to any one of the preceding claims, wherein the product comprising the pharmaceutical active agent comprises a transdermal patch comprising the pharmaceutical active agent.

6. A packaged pharmaceutical product, comprising:
a film according to claim 1, wherein the film has a total thickness of from about 1.0 to 10 mils, wherein the product-contacting sealing layer defines a sealed interior volume; and
the product comprising a pharmaceutical active agent disposed in the interior volume of the sealed package, wherein the pharmaceutical agent is in contact with the sealing layer.

7. A method for packaging a pharmaceutical product comprising a pharmaceutical active agent, the method comprising:
sealing the pharmaceutical product in an interior of a packaging film, wherein the film comprises a sealing layer comprising at least 90 wt. % of an ethylene norbornene copolymer having a glass transition temperature in a range from 65° C. to 110° C.,
wherein the pharmaceutical active agent comprises one or more of fentanyl, nicotine, estradiol, clonidine, ethinyl estradiol, buprenorphine, granisitron, and scopolamine;
wherein sealing the pharmaceutical product in the interior of the packaging film comprises placing the pharmaceutical agent in contact with the sealing layer, and
wherein the pharmaceutical active agent comprises a Hansen Solubility Parameter for the polymeric sealing layer of 0.5 or greater.

8. A method according to claim 7, wherein the pharmaceutical active agent comprises a Hansen Solubility Parameter for the polymeric sealing layer of 1 or greater.

9. A method according to claim 7, wherein the sealing layer comprises at least 95 wt. % ethylene norbornene copolymer.

10. A packaged pharmaceutical product comprising:
a drug resistant, flexible, multilayer packaging film comprising a drug contact layer having at least 90 wt. % of an ethylene norbornene copolymer having a glass transition temperature of from 55° C. to 110° C., wherein the film is formed into a flexible container;
a product comprising a pharmaceutical active agent, wherein the pharmaceutical active agent comprises one or more of fentanyl, nicotine, estradiol, clonidine, ethinyl estradiol, buprenorphine, granisitron, and scopolamine;
wherein the pharmaceutical active agent is in contact with the drug contact layer of the film and wherein the pharmaceutical active agent comprises a Hansen Solubility Parameter for the drug contacting layer of 0.7 or greater.

11. The packaged pharmaceutical product according to claim 10, wherein the product comprising the pharmaceutical active agent comprises a transdermal patch comprising the pharmaceutical active agent and wherein the transdermal patch is a nicotine or fentanyl drug delivery patch.

* * * * *

UNITED STATES PATENT AND TRADEMARK OFFICE
CERTIFICATE OF CORRECTION

PATENT NO. : 10,934,070 B2
APPLICATION NO. : 15/115993
DATED : March 2, 2021
INVENTOR(S) : Jennifer L. Riis et al.

Page 1 of 1

It is certified that error appears in the above-identified patent and that said Letters Patent is hereby corrected as shown below:

In the Claims

Column 32, Line 58: Claim 1 delete "product-containing" and insert -- product-contacting --.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*